United States Patent
Johanek

(10) Patent No.: US 11,083,896 B2
(45) Date of Patent: Aug. 10, 2021

(54) HIGH DUTY CYCLE ELECTRICAL STIMULATION THERAPY

(71) Applicant: Medtronic, Inc., Minneapolis, MN (US)

(72) Inventor: Lisa M. Johanek, White Bear Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 182 days.

(21) Appl. No.: 16/062,959

(22) PCT Filed: Dec. 15, 2016

(86) PCT No.: PCT/US2016/066991
§ 371 (c)(1),
(2) Date: Jun. 15, 2018

(87) PCT Pub. No.: WO2017/106539
PCT Pub. Date: Jun. 22, 2017

(65) Prior Publication Data
US 2018/0369593 A1 Dec. 27, 2018

Related U.S. Application Data

(60) Provisional application No. 62/269,768, filed on Dec. 18, 2015.

(51) Int. Cl.
*A61N 1/36* (2006.01)

(52) U.S. Cl.
CPC ..... *A61N 1/36175* (2013.01); *A61N 1/36062* (2017.08); *A61N 1/36071* (2013.01);
(Continued)

(58) Field of Classification Search
USPC .......................................................... 607/2
See application file for complete search history.

(56) References Cited

U.S. PATENT DOCUMENTS

| 5,603,726 A | 2/1997 | Schulman et al. |
| 5,800,465 A | 9/1998 | Thompson et al. |

(Continued)

FOREIGN PATENT DOCUMENTS

| CN | 102921105 B | 8/2015 |
| CN | 107050645 A | 8/2017 |

(Continued)

OTHER PUBLICATIONS

International Preliminary Report on Patentability from International Application No. PCT/US2016/066991, dated Jun. 28, 2018, 7 pp.
(Continued)

*Primary Examiner* — Nicole F Lavert
(74) *Attorney, Agent, or Firm* — Shumaker & Sieffert, P.A.

(57) ABSTRACT

In some examples, a medical device is configured to deliver high dose electrical stimulation therapy to a patient by at least generating and delivering an electrical stimulation signal having a relatively high duty cycle, and a stimulation intensity less than a perception or paresthesia threshold intensity level for the patient. The pulses may each have a relatively low amplitude, but due at least in part to a relatively high number of pulses per unit of time, the electrical stimulation signal may be high enough to elicit a therapeutic response from the patient. In some examples, the plurality of pulses may have a duty cycle in a range of about 5% to about 50%. Following the generation and delivery of the plurality of pulses, one or more recharge pulses for the plurality of pulses may be delivered.

21 Claims, 10 Drawing Sheets

(52) U.S. Cl.
CPC ..... *A61N 1/36167* (2013.01); *A61N 1/36171* (2013.01); *A61N 1/36178* (2013.01); *A61N 1/36007* (2013.01); *A61N 1/3615* (2013.01); *A61N 1/36064* (2013.01); *A61N 1/36067* (2013.01); *A61N 1/36107* (2013.01)

(56) References Cited

U.S. PATENT DOCUMENTS

| | | |
|---|---|---|
| 6,289,247 B1 | 9/2001 | Faltys et al. |
| 6,314,325 B1 | 11/2001 | Fitz |
| 6,421,566 B1 | 7/2002 | Holsheimer |
| 6,505,078 B1 | 1/2003 | King et al. |
| 6,675,046 B2 | 1/2004 | Holsheimer |
| 6,850,802 B2 | 2/2005 | Holsheimer |
| 6,988,006 B2 | 1/2006 | King et al. |
| 7,333,858 B2 | 2/2008 | Killian et al. |
| 7,577,480 B2 | 8/2009 | Zeijlemaker |
| 7,657,318 B2 | 2/2010 | King et al. |
| 7,689,289 B2 | 3/2010 | King |
| 7,742,810 B2 | 6/2010 | Moffitt et al. |
| 8,359,103 B2 | 1/2013 | Alataris et al. |
| 8,504,150 B2 | 8/2013 | Skelton |
| 8,620,441 B2 | 12/2013 | Greenberg et al. |
| 8,694,108 B2 | 4/2014 | Alataris et al. |
| 8,708,934 B2 | 4/2014 | Skelton et al. |
| 8,712,533 B2 | 4/2014 | Alataris et al. |
| 8,712,534 B2 | 4/2014 | Wei |
| 9,002,460 B2 | 4/2015 | Parker |
| 9,138,582 B2 | 9/2015 | Doan et al. |
| 9,155,892 B2 | 10/2015 | Parker et al. |
| 9,339,655 B2 | 5/2016 | Carbunaru |
| 9,381,356 B2 | 7/2016 | Parker et al. |
| 9,386,934 B2 | 7/2016 | Parker et al. |
| 2004/0267333 A1 | 12/2004 | Kronberg |
| 2007/0067004 A1 | 3/2007 | Boveja et al. |
| 2008/0221640 A1 | 9/2008 | Overstreet et al. |
| 2009/0036945 A1 | 2/2009 | Chancellor et al. |
| 2009/0204173 A1* | 8/2009 | Fang .................. A61N 1/36171 607/46 |
| 2009/0222053 A1 | 9/2009 | Gaunt et al. |
| 2011/0054570 A1 | 3/2011 | Lane |
| 2011/0071589 A1 | 3/2011 | Starkebaum et al. |
| 2011/0125223 A1 | 5/2011 | Carbunaru et al. |
| 2011/0282412 A1 | 11/2011 | Glukhovsky et al. |
| 2012/0130444 A1 | 5/2012 | Wei et al. |
| 2012/0155188 A1 | 6/2012 | Buettner et al. |
| 2012/0296389 A1 | 11/2012 | Fang et al. |
| 2013/0060301 A1 | 3/2013 | Polefko et al. |
| 2013/0079841 A1* | 3/2013 | Su ...................... A61N 1/36007 607/41 |
| 2013/0110194 A1 | 5/2013 | Wei et al. |
| 2013/0208390 A1 | 8/2013 | Singh et al. |
| 2013/0268021 A1 | 10/2013 | Moffitt |
| 2013/0289664 A1 | 10/2013 | Johanek |
| 2014/0005753 A1 | 1/2014 | Carbunaru |
| 2014/0025146 A1 | 1/2014 | Alataris et al. |
| 2014/0031896 A1 | 1/2014 | Alataris et al. |
| 2014/0031905 A1 | 1/2014 | Irazoqui et al. |
| 2014/0074189 A1 | 3/2014 | Moffitt |
| 2014/0142549 A1* | 5/2014 | Su ...................... A61K 31/165 604/512 |
| 2014/0142656 A1 | 5/2014 | Alataris et al. |
| 2014/0142673 A1 | 5/2014 | Alataris et al. |
| 2014/0243924 A1 | 8/2014 | Zhu et al. |
| 2014/0243926 A1 | 8/2014 | Carcieri |
| 2014/0277281 A1 | 9/2014 | Grandhe |
| 2014/0296936 A1 | 10/2014 | Alataris et al. |
| 2014/0364920 A1 | 12/2014 | Doan et al. |
| 2014/0371813 A1 | 12/2014 | King et al. |
| 2014/0378941 A1 | 12/2014 | Su et al. |
| 2014/0379043 A1 | 12/2014 | Howard |
| 2015/0127062 A1 | 5/2015 | Holley |
| 2015/0179177 A1 | 6/2015 | Nagao |
| 2015/0360031 A1 | 12/2015 | Bornzin et al. |
| 2016/0030741 A1 | 2/2016 | Wei et al. |
| 2016/0082265 A1 | 3/2016 | Moffitt et al. |
| 2016/0114166 A1 | 4/2016 | Kaula et al. |
| 2016/0121124 A1 | 5/2016 | Johanek et al. |
| 2016/0136420 A1 | 5/2016 | Brink et al. |
| 2016/0157769 A1 | 6/2016 | Min et al. |
| 2016/0175594 A1 | 6/2016 | Min et al. |
| 2016/0271413 A1 | 9/2016 | Vallejo et al. |
| 2017/0209695 A1 | 7/2017 | Solomon |
| 2018/0056073 A1 | 3/2018 | Torgerson |

FOREIGN PATENT DOCUMENTS

| | | |
|---|---|---|
| EP | 2396072 B1 | 3/2013 |
| WO | 2002009808 A1 | 2/2002 |
| WO | 2010058178 A1 | 5/2010 |
| WO | 2010123704 A | 10/2010 |
| WO | 2011156286 A2 | 12/2011 |
| WO | 2015143509 A1 | 1/2015 |
| WO | 2015179177 A1 | 11/2015 |
| WO | 2015179281 A1 | 11/2015 |
| WO | 2016090420 A1 | 6/2016 |
| WO | 2017106503 A1 | 6/2017 |

OTHER PUBLICATIONS

"St. Jude's Prodigy Neurostimulator with Burst Technology," Medgadget, Mar. 20, 2014, 4 pp.

Abejon et al., "Back pain coverage with spinal cord stimulation: A different treatment for each patient," International Neuromodulation Society. Jun. 10, 2015; 567, Abstract Only, 1 pp.

Abeloos, et al., "High density stimulation as an alternative to uncomfortable cervical tonic spinal cord stimulation: case report," International Neuromodulation Society 12th World Congress, Jun. 11-15, 2015, Abstract Only, 1 pp.

Breel, et al., "High Density Stimulation: A novel programming paradigm for the treatment of chronic pain," International Neuromodulation Society (INS) 12th World Congress; Jun. 9, 2015, Abstract Only, 1 pp.

Cuellar MD et al., "Effect of high-frequency alternating current on spinal afferent nociceptive transmission," Neuromodulation: Technology at the Neural Interface; Jul.-Aug. 2013;16(4): pp. 318-327.

Cui, et al., "Effect of spinal cord stimulation on tactile hypersensitivity in mononeuropathic rats is potentiated by simultaneous GABA(B) and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

De Ridder, et al., "Burst spinal cord stimulation for limb and back pain," World neurosurgery, Nov. 2013; 80(5):642-649 e641.

De Ridder, et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak, MD, et al., "High density stimulation: a novel programming paradigm for the treatment of chronic back and leg pain," Abstracts, International Neuromodulation Society 12th World Congress: Jun. 11-15, 2015, 1 pp.

Sao et al., "Effects of spinal cord stimulation with "standard clinical" and higher frequencies on peripheral blood flow in rats," Brain Res. Feb. 8, 2010;1313: pp. 53-61.

Grider, et al., "High Frequency (1000 Hz) Stimulation Using Commercially Available Implantable Pulse Generator," North American Neuromodulation Society. Dec. 2013, Abstract Only, 2 pp.

Guan et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.

Guan et al., "Spinal Cord Stimulation: Neurophysiological and Neurochemical Mechanisms of Action" Curr Pain Headache Rep DOI 10,1007s11916-014-0260-4, Mar. 2012, pp. 217-225.

Holsheimer, "Computer modelling of spinal cord stimulation and its contribution to therapeutic efficacy," Spinal Cord Aug. 1998, 36: pp. 531-540.

(56) References Cited

OTHER PUBLICATIONS

Hunt SP, Mantyh PW. The molecular dynamics of pain control. Nat Rev Neurosci. Feb. 2001;2(2):83-91.
Kemler, et al., "Spinal cord stimulation in patients with chronic reflex sympathetic dystrophy," N Engl J Med, Aug. 31, 2000; 343(9):618-624.
Kilgore, PhD, et al., "Reversible Nerve Conduction Block Using Kilohertz Frequency Alternating Current," Neuromodulation. Aug. 2013, pp. 242-255.
Kumar, et al., "Spinal cord stimulation versus conventional medical management for neuropathic pain: a multicentre randomised controlled trial in patients with failed back surgery syndrome," Pain Jul. 2007; 132(1-2): 179-188.
Likar et al., "High density spinal cord stimulation: a multi-center experience," Abstracts, International Neuromodulation Society 12th World Congress; Jun. 11-15, 2015, 1 pp.
Sweet et al., "High Frequency vs. Burst Stimulation Patterns for Dorsal Column Stimulation: The Importance of Charge," American Association of Neurological Surgeons, Abstract, Apr. 4, 2014, 2 pp.
Maeda, et al., "Low frequencies, but not high frequencies of bi-polar spinal cord stimulation reduce cutaneous and muscle hyperalgesia induced by nerve injury," Pain; Feb. 2008; 138(1): pp. 143-152.
North MD. et al., "Spinal cord stimulation versus repeated lumbosacral spine surgery for chronic pain: a randomized, controlled trial," Neurosurgery, Jan. 2005; 56(1): 98-106; discussion 106-107.
North, et al., "Clinical outcomes of 1 kHz subperception spinal cord stimulation (SCS): Results of a prospective randomized controlled crossover trial," Abstracts, International Neuromodulation Society, Jun. 2015, 1 pp.
Ranck Jr., et al., "Which elements are excited in electrical stimulation of mammalian central nervous system: a review," Brain Res. Nov. 21, 1975; 98(3): pp. 417-440.
Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Sato, et al., "Spinal cord stimulation reduces hypersensitivity through activation of opioid receptors in a frequency-dependent manner," Eur J Pain. Apr. 17, 2012 (4): pp. 551-561.
Song, et al., "Efficacy of kilohertz-frequency and conventional spinal cord stimulation in rat models of different pain conditions," Neuromodulation Jan. 2014; 17(3): pp. 226-234.
Schu et al., "A prospective, randomised, double-blind, placebo-controlled study to examine the effectiveness of burst spinal cord stimulation patterns for the treatment of failed back surgery syndrome," Neuromodulation. Jun. 2014; 17(5):443-450.
Shechter et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the affective U.S. filing date of the present application, and any foreign priority date that the particular month of publication is not in issue.
Maeda, et al., "Increased c-fos immunoreactivity in the spinal cord and brain following spinal cord stimulation is frequency-dependent," Brain Res. Mar. 9, 2009;1259: pp. 40-50.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith, et al., "Successful use of high-frequency spinal cord stimulation following traditional treatment failure," Stereotact Funct Neurosurg. Apr. 2015; 93(3): pp. 190-193.
Wille, MD, et al., "Altering Conventional to High Density Spinal Cord Stimulation: An Energy Dose-Response Relationship in Neuropathic Pain Therapy," Neuromodulation: Technology at the Neural Interface, Aug. 2016, 9 pp.
Maggi, et al., "Effect of urethane anesthesia on the micturition reflex in capsaicin-lreated rats." Journal of the Autonomic Nervous System, Jan. 1990, 30(3): 247-251.
Walter, et al., "Inhibiting the hyperreflexic bladder with electrical stimulation in a spinal animal model." Neurourology and Urodynamics, 1993, 12:241-253. Applicant points out in accordance with MPEP 609.04(a) that the 1993 year of publication is sufficiently earlier than the effective U.S. filing date of the present application, and any foreign priority date that the particular month of publication is not in issue.
Hubscher, et al., "Convergence and cross talk in urogenital neural circuitries," J. Neurophysiol 110: 1997-2005, first published Aug. 7, 2013, 9 pp.
Snellings et al., "Effects of stimulation site and stimulation parameters on baldder inhibition by electrical nerve stimulation," BJU International, published Aug. 9, 2011, pp. 136-143.
Woock, et al., "Activation and inhibition of the micturition reflex by penile afferents in the cat," Am J. Physiol Regul Intergre Comp Physiol, published Apr. 23, 2008, pp. R1880-R1889.
Bhadra et al., "High frequency electrical conduction block of the pudendal nerve," Journal of Neural Eng., IOP Publishing LTD, published Jun. 3, 2006,14 pp.
Boger et al., "Bladder Voiding by Combined High Frequency Electrical Pudendal Nerve Block and Sacral Root Stimulation," Neurourology and Urodynamics, Wiley InterScience, vol. 27, Issue 5, Jul. 2, 2008, 6 pp.
U.S. Appl. No. 16/061,930, filed by Lisa M. Johanek, filed Dec. 15, 2016.
International Search Report and Written Opinion from International Application No. PCT/US2016/066991, dated Feb. 27, 2017, 10 pp.
U.S. Appl. No. 15/623,141, filed by Nathan A. Torgeson, filed Jun. 14, 2017.
Office Action from U.S. Appl. No. 16/061,930, dated Jan. 8, 2021, 12 pp.
Amendment in Response to Office Action dated Jan. 8, 2021, from U.S. Appl. No. 16/061,930, filed Apr. 8, 2021, 14 pp.

* cited by examiner

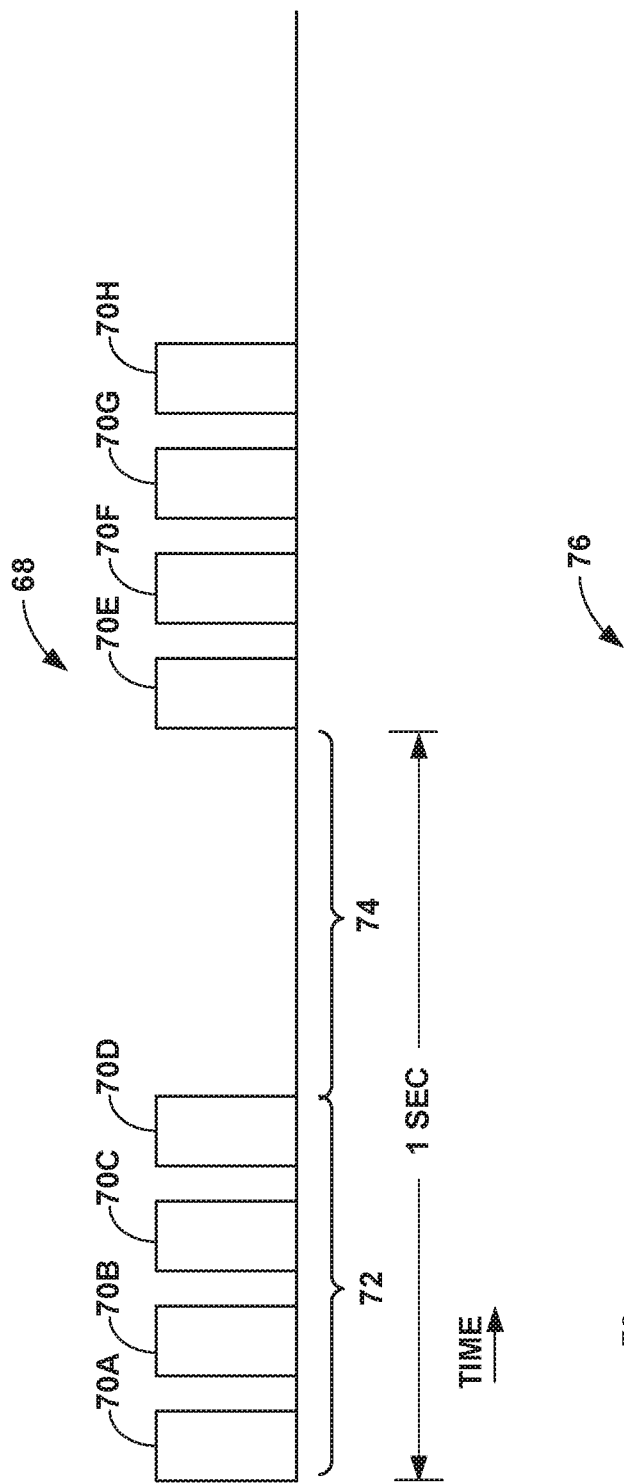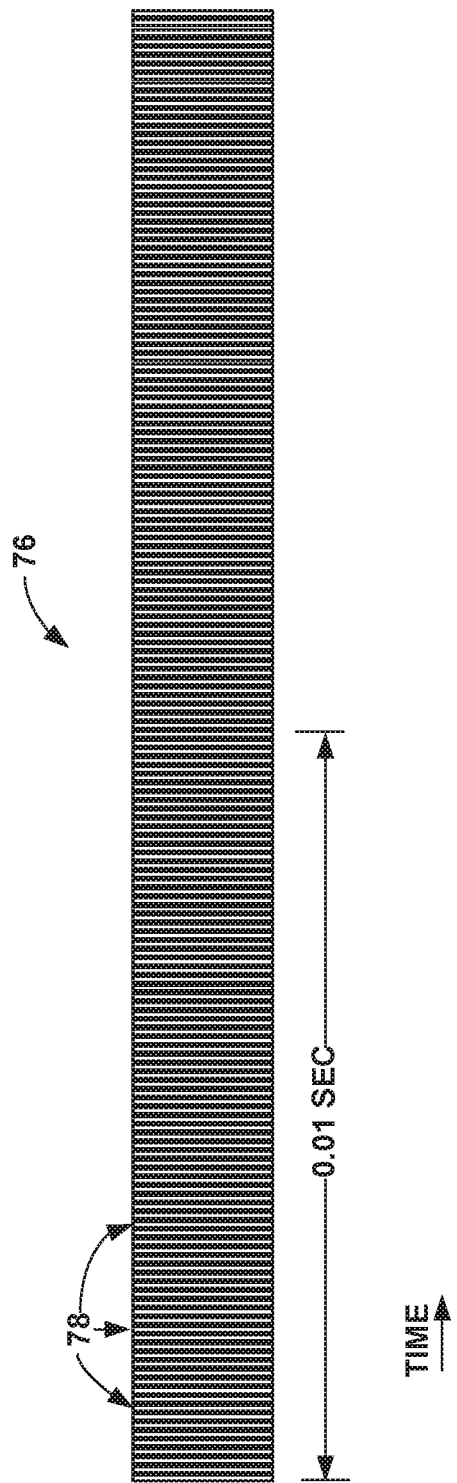

HIGH DUTY CYCLE ELECTRICAL STIMULATION THERAPY

RELATED APPLICATIONS

This application is a U.S. National Stage filing under 35 U.S.C. 371 of International Application No. PCT/US2016/066991, filed Dec. 15, 2016, which claims the benefit of U.S. Provisional Application No. 62/269,768, which was on filed Dec. 18, 2015 and is entitled, "HIGH DUTY CYCLE ELECTRICAL STIMULATION THERAPY," the entire content of which is incorporated herein by reference.

TECHNICAL HELD

The disclosure relates to electrical stimulation therapy.

BACKGROUND

Medical devices may be external or implanted, and may be used to deliver electrical stimulation therapy to patients to various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient.

SUMMARY

This disclosure describes example medical devices, systems, and techniques for delivering a relatively high dose of electrical stimulation therapy to a patient per unit of time to treat one or more patient conditions. In some examples, a medical device is configured to deliver the high dose of electrical stimulation therapy by at least generating and delivering an electrical stimulation signal having a relatively high duty cycle, and stimulation intensity less than a perception or paresthesia threshold intensity level of the patient. The electrical stimulation therapy may comprise a plurality of stimulation pulses that may each have relatively low amplitude. Due at least in part to a relatively high number of pulses per unit of time (e.g., per second) and the resulting relatively high energy delivery per unit of time, the electrical stimulation delivered to the patient may be high enough to elicit a therapeutic response from the patient.

In some examples, the electrical stimulation may have a duty cycle in a range of about 5% to about 50%. A medical device implanted in a patient may generate a first electrical stimulation pulse and then deliver the first electrical stimulation pulse to the patient. Subsequent to delivering the first electrical stimulation pulse, the medical device may generate and deliver a second electrical stimulation pulse to the patient. Subsequent to delivering the second electrical stimulation pulse, the medical device may deliver one or more recharge signals (e.g., one or more pulses or other waveforms) for the first and second electrical stimulation pulses. The one or more recharge signals may balance the electrical charge in tissue created by the first and second electrical stimulation pulses. In this way, the medical device may deliver one or more recharge pulses to the patient after delivering a plurality of pulses of the electrical stimulation signal having the relatively high duty cycle. In some examples, each electrical stimulation pulse has a first polarity and the recharge signal has a second polarity that is opposite to the first polarity. In certain examples, the one or more recharge signals may be withheld for a period of time after delivery of previous electrical stimulation pulses before being delivered.

In some examples, the electrical stimulation may have a frequency in a range about 1 Hertz (Hz) to about 1400 Hz, such as less than about 1000 Hz, and each of the pulses may have a pulse width less than or equal to about 5 milliseconds (ms), such as in a range of about 0.1 ms to about 5 ms, or in a range of about 0.1 ms to about 1 ms. In these examples, the frequency and pulse width may be selected such that the electrical stimulation may have a duty cycle in a range of about 5% to about 50%. In addition, the frequency, amplitude, and pulse width may be selected such that the stimulation intensity less than at least one of a perception threshold intensity level or a paresthesia threshold intensity level of the patient.

In one example, a method includes generating, by a medical device, an electrical stimulation signal comprising a plurality of pulses and having a duty cycle in a range of about 5% to about 50% and a frequency in a range of about 1 Hertz to about 1400 Hertz, wherein each of the pulses has a pulse width in a range of about 0.1 millisecond to about 5 milliseconds, the electrical stimulation signal having a stimulation intensity less than of at least one of a perception threshold or a paresthesia threshold of a patient; and delivering, by the medical device, the electrical stimulation signal to the patient.

In another example, a method comprises generating, by a medical device, a first electrical stimulation signal according to a first therapy program, the first electrical stimulation signal comprising a first plurality of electrical stimulation pulses; generating, by the medical device, a second electrical stimulation signal according to a second therapy program, the second electrical stimulation signal comprising a second plurality of electrical stimulation pulses, wherein each pulse of the first and second electrical stimulation signals has a pulse width in a range of about 0.1 millisecond to about 5 milliseconds; delivering, by the medical device, the first and second electrical stimulation signals to a patient via respective subsets of electrodes to generate first and second stimulation fields; and delivering, by the medical device, a recharge signal following the delivery of at least one pulse of each of the first and second electrical stimulation signals. Delivering the first and second electrical stimulation signals comprises interleaving delivery of the first and second electrical stimulation signals to deliver electrical stimulation pulses at a frequency in a range of about 1 Hertz to about 1400 Hertz. The first and second stimulation fields, individually and when overlapping, have stimulation intensities less than at least one of: a perception threshold or a paresthesia threshold of the patient.

In another example, a method comprises determining a paresthesia or perception threshold for a patient; determining, for a selected frequency, a strength-duration curve based on the paresthesia or perception threshold; and determining, based on the strength-duration curve, a set of one or more electrical stimulation parameter values for generating an electrical stimulation signal having stimulation intensity less than at least one of the perception threshold or the paresthesia threshold of the patient, and having a duty cycle in a range of about 5% to about 50%, a frequency in a range of about 1 Hertz to about 1400 Hertz, and a pulse width in a range of about 0.1 millisecond to about 5 milliseconds.

In another example, stimulation generating circuitry configured to generate and deliver electrical stimulation therapy to a patient; and processing circuitry configured to control the stimulation generating circuitry to generate and deliver an electrical stimulation signal comprising a plurality of pulses and having a duty cycle in a range of about 5% to about 50% and a frequency in a range of about 1 Hertz to about 1400 Hertz, wherein each of the pulses has a pulse width in a range of about 0.1 millisecond to about 5 milliseconds, the electrical stimulation signal having a stimulation intensity less than at least one of a perception threshold or a paresthesia threshold of the patient.

In another example, a system comprises a plurality of electrodes; stimulation generating circuitry configured to generate and deliver electrical stimulation therapy to a patient via one or more subset of the electrodes; and processing circuitry configured to control the stimulation generating circuitry to generate a first electrical stimulation signal according to a first therapy program, the first electrical stimulation signal comprising a first plurality of electrical stimulation pulses, generate a second electrical stimulation signal according to a second therapy program, the second electrical stimulation signal comprising a second plurality of electrical stimulation pulses, wherein each pulse of the first and second electrical stimulation signals has a pulse width in a range of about 0.1 millisecond to about 5 milliseconds, deliver the first and second electrical stimulation signals to a patient via respective subsets of electrodes to generate first and second stimulation fields, wherein the processing circuitry is configured to control the stimulation generating circuitry to deliver the first and second electrical stimulation signals by at least interleaving delivery of the first and second electrical stimulation signals to deliver electrical stimulation pulses at a frequency in a range of about 1 Hertz to about 1400 Hertz, and deliver a recharge signal following the delivery of at least one pulse of each of the first and second electrical stimulation signals. The first and second stimulation fields, individually and when overlapping, have stimulation intensities less than at least one of: a perception threshold or a paresthesia threshold of the patient.

In another example, a system comprises processing circuitry configured to determine a paresthesia or perception threshold stimulation intensity level of a patient, determine, for a selected frequency, a strength-duration curve based on the paresthesia or perception threshold stimulation intensity level, and determine, based on the strength-duration curve, a set of one or more electrical stimulation parameter values for generating an electrical stimulation signal having stimulation intensity less than at least one of the perception threshold or the paresthesia threshold of the patient, and having a duty cycle in a range of about 5% to about 50%, a frequency in a range of about 1 Hertz to about 1400 Hertz, and a pulse width in a range of about 0.1 millisecond to about 5 milliseconds.

In another example, a system includes means for generating an electrical stimulation signal comprising a plurality of pulses and having a duty cycle in a range of about 5% to about 50% and a frequency in a range of about 1 Hertz to about 1400 Hertz, wherein each of the pulses has a pulse width in a range of about 0.1 millisecond to about 5 milliseconds, the electrical stimulation signal having a stimulation intensity less than at least one of a perception threshold or a paresthesia threshold of a patient; and means for delivering the electrical stimulation signal to the patient.

In another example, a system includes means for generating a first electrical stimulation signal according to a first therapy program, the first electrical stimulation signal comprising a first plurality of electrical stimulation pulses, and a second electrical stimulation signal according to a second therapy program, the second electrical stimulation signal comprising a second plurality of electrical stimulation pulses, wherein each pulse of the first and second electrical stimulation signals has a pulse width in a range of about 0.1 millisecond to about 5 milliseconds; means for delivering the first and second electrical stimulation signals to a patient via respective subsets of electrodes to generate first and second stimulation fields, wherein the means for delivering delivers the first and second electrical stimulation signals by at least interleaving delivery of the first and second electrical stimulation signals to deliver electrical stimulation pulses at a frequency in a range of about 1 Hertz to about 1400 Hertz; and means for delivering a recharge signal following the delivery of at least one pulse of each of the first and second electrical stimulation signals. The first and second stimulation fields, individually and when overlapping, have stimulation intensities less than at least one of: a perception threshold or a paresthesia threshold of the patient.

In another example, a system includes means for determining a paresthesia or perception threshold for a patient; means for determining, for a selected frequency, a strength-duration curve based on the paresthesia or perception threshold; and means for determining, based on the strength-duration curve, a set of one or more electrical stimulation parameter values for generating an electrical stimulation signal having stimulation intensity less than at least one of the perception threshold or the paresthesia threshold of the patient, and having a duty cycle in a range of about 20% to about 50%, a frequency in a range of about 1 Hertz to about 1400 Hertz, and a pulse width in a range of about 0.1 millisecond to about 5 milliseconds.

In another example, a computer-readable storage medium comprises instructions that, when executed by processing circuitry, cause the processing circuitry to: control stimulation generating circuitry to generate an electrical stimulation signal comprising a plurality of pulses and having a duty cycle in a range of about 5% to about 50% and a frequency in a range of about 1 Hertz to about 1400 Hertz, wherein each of the pulses has a pulse width in a range of about 0.1 millisecond to about 5 milliseconds, the electrical stimulation signal having a stimulation intensity less than at least one of a perception threshold or a paresthesia threshold of a patient; and control the stimulation generating circuitry to deliver the electrical stimulation signal to the patient.

In another example, a computer-readable storage medium comprises instructions that, when executed by processing circuitry, cause the processing circuitry to control stimulation generating circuitry of a medical device to generate a first electrical stimulation signal according to a first therapy program, the first electrical stimulation signal comprising a first plurality of electrical stimulation pulses; control the stimulation generating circuitry of the medical device to generate a second electrical stimulation signal according to a second therapy program, the second electrical stimulation signal comprising a second plurality of electrical stimulation pulses, wherein each pulse of the first and second electrical stimulation signals has a pulse width in a range of about 0.1 millisecond to about 5 milliseconds; control the stimulation generating circuitry to deliver the first and second electrical stimulation signals to a patient via respective subsets of electrodes to generate first and second stimulation fields by at least interleaving delivery of the first and second electrical stimulation signals to deliver electrical stimulation pulses at a frequency in a range of about 1 Hertz to about 1400 Hertz; and control the stimulation generating circuitry to deliver a recharge signal following the delivery of at least one pulse of each of the first and second electrical stimulation signals. The first and second stimulation fields, individually and when overlapping, have stimulation intensities less than at least one of: a perception threshold or a paresthesia threshold of the patient.

In another example, a system may include a plurality of electrodes and stimulation generation circuitry configured to generate and deliver electrical stimulation therapy to a patient. The system may further include processing circuitry configured to control the stimulation generation circuitry. The processing circuitry may have the stimulation generation circuitry generate a plurality of electrical stimulation pulses having a duty cycle in a range of about 5% to about 50%. The plurality of electrical stimulation pulses may have a stimulation intensity less than at least one of a perception threshold or a paresthesia threshold of a patient. The processing circuitry may have the stimulation generation circuitry deliver a first electrical stimulation pulse of the plurality of electrical stimulation pulses to the patient. The processing circuitry may have the stimulation generation circuitry deliver a second electrical stimulation pulse of the plurality of electrical stimulation pulses to the patient after delivering the first electrical stimulation pulse. The processing circuitry may have the stimulation generation circuitry deliver one or more recharge pulses for at least the first electrical stimulation pulse and the second electrical stimulation pulse after delivering the first pulse and the second pulse.

In another example, a computer-readable storage medium comprises instructions that, when executed by processing circuitry, cause the processing circuitry to: determine a paresthesia or perception threshold for a patient; determine, for a selected frequency, a strength-duration curve based on the paresthesia or perception threshold; and determine, based on the strength-duration curve, a set of one or more electrical stimulation parameter values for generating an electrical stimulation signal having stimulation intensity less than at least one of the perception threshold or the paresthesia threshold of the patient, and having a duty cycle in a range of about 5% to about 50%, a frequency in a range of about 1 Hertz to about 1400 Hertz, and a pulse width in a range of about 0.1 millisecond to about 5 milliseconds. In another aspect, the disclosure is directed to a computer-readable storage medium, which may be an article of manufacture. The computer-readable storage medium includes computer-readable instructions for execution by one or more processors. The instructions cause one or more processors to perform any part of the techniques described herein. The instructions may be, for example, software instructions, such as those used to define a software or computer program. The instructions may cause the processor to generate a plurality of electrical stimulation pulses having a duty cycle in a range of about 5% to about 50%. The plurality of electrical stimulation pulses may have a stimulation intensity less than at least one of a perception threshold or a paresthesia threshold of a patient. The instructions may further cause the processor to deliver a first electrical stimulation pulse of the plurality of electrical stimulation pulses to the patient. The instructions may further cause the processor to deliver a second electrical stimulation pulse of the plurality of electrical stimulation pulses to the patient after delivering the first electrical stimulation pulse. The instructions may further cause the processor to deliver one or more recharge pulses for at least the first electrical stimulation pulse and the second electrical stimulation pulse after delivering the first pulse and the second pulse.

BRIEF DESCRIPTION OF DRAWINGS

FIG. 6 illustrates an example burst electrical stimulation waveform.

FIG. 7 illustrates an example high frequency electrical stimulation waveform.

DETAILED DESCRIPTION

Figure 1:
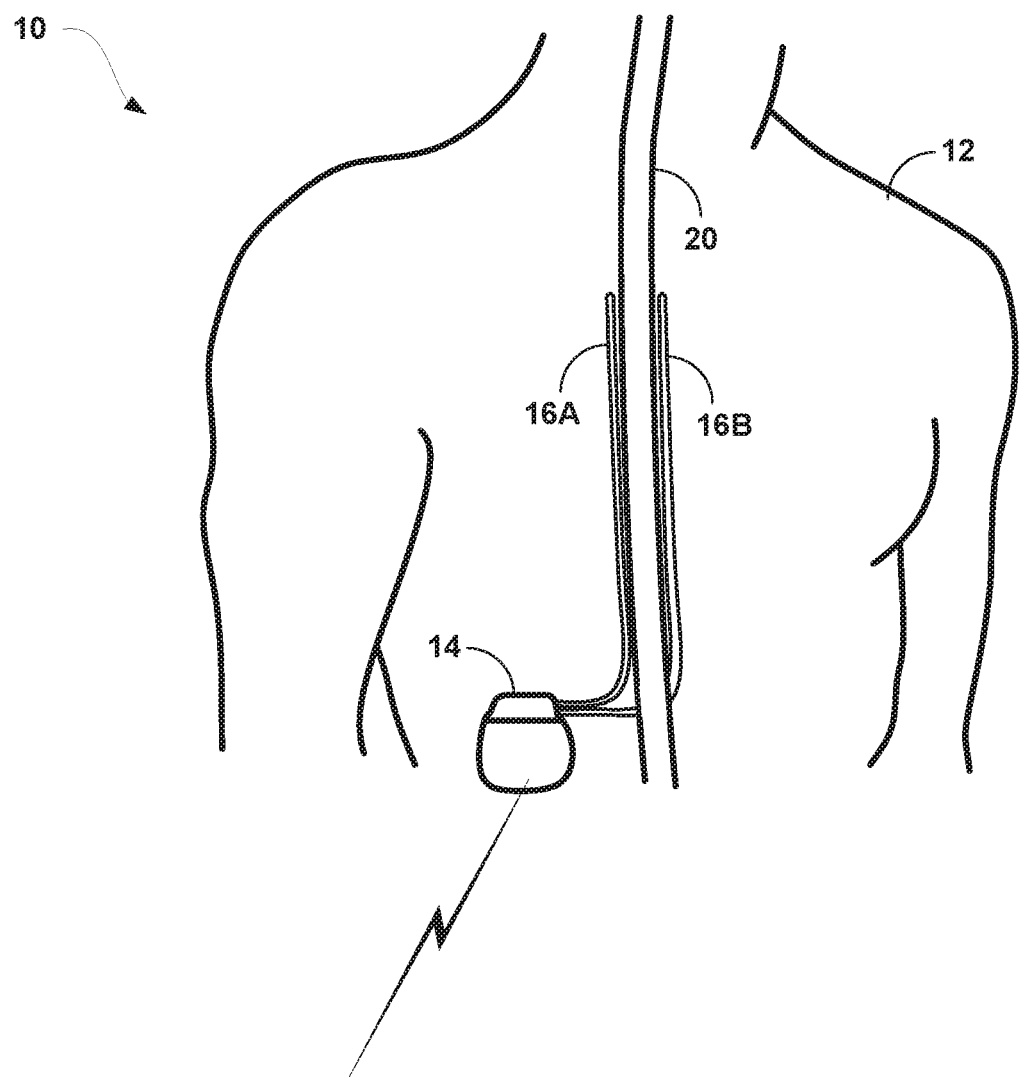
FIG. 1 is a conceptual diagram illustrating an example system that includes a medical device programmer and an implantable medical device (IMD) configured to deliver high dose electrical stimulation therapy to a patient.

This disclosure describes example medical devices, systems, and techniques for delivering electrical stimulation therapy to treat one or more patient conditions, the electrical stimulation therapy providing a relatively high amount of electrical stimulation per unit of time (referred to herein as a "high dose") and a stimulation intensity less than a perception or paresthesia threshold intensity level of the patient. The dose of electrical stimulation may be a function of a frequency and pulse width of the pulses. The electrical stimulation therapy may include a plurality of pulses, such as a first set of one or more pulses that charge tissue (e.g., electrical stimulation pulses) and a second set of one or more pulses that balance the charge in the tissue (e.g., recharge signal or recharge pulses). Subsequent to the system generating and delivering all of the plurality of electrical stimulation pulses, the system may deliver one or more recharge signals (or recharge pulses) for the plurality of pulses. The perception threshold intensity level may be the lowest determined stimulation intensity level at which a patient perception of the electrical stimulation occurs, and the paresthesia threshold intensity level may be the lowest determined stimulation intensity level at which the electrical stimulation causes paresthesia, for example, within a predetermined time range (e.g., 30 seconds) of the patient receiving the electrical stimulation.

The high dose of electrical stimulation therapy described herein delivers a relatively high amount of energy (e.g., electrical charge) to tissue of the patient per unit of time (e.g., one second). For example, the high dose of electrical stimulation therapy may have a charge delivery of about 100 microCoulombs to about 2,000 microCoulombs per second. The sufficiency of electrical stimulation in producing a desired therapeutic effect may be based on the amount of charge delivered to the tissue of the patient per unit of time. In the case of electrical stimulation pulses (hereinafter interchangeably referred to as either "electrical stimulation pulses" or "electrical pulses" or "pulses"), the amount of charge delivered to the tissue of the patient per unit of time may be calculated by multiplying the electrical current delivered during an electrical pulse by the pulse width, which yields the amount of electrical charge delivered during a single pulse, and multiplying the amount of electrical charge delivered to the patient for one pulse by the frequency of the electrical stimulation signal.

The high energy dose electrical stimulation described herein may be provided by an electrical stimulation signal having a relatively high duty cycle. The duty cycle may be, for example, the percentage of active electrical stimulation per unit of time (e.g., one second), and may, for example, be a product of a frequency of the pulses and a pulse width of the pulses. Thus, the duty cycle may, in some examples, by defined by a plurality of pulses per unit of time, rather than a single pulse. However, other waveforms may be used in other examples.

In some examples, a medical device is configured to generate and deliver, via one or more electrodes, an electrical stimulation signal having a high duty cycle and a frequency less than or equal to about 1400 Hertz (Hz), such as less than or equal to about 1000 Hz. The frequency may, for example, be in a range of about 1 Hz to about 1400 Hz, such as about 1000 Hz. The pulses may each have a relatively low amplitude (e.g., about 1 milliamp (mA) to about 25 mA, such as about 1 mA to about 5 mA), which can be the same or may vary between the pulses. In some examples, the duty cycle may be greater than 5% such as in a range of about 5% to about 50%, or about 20% to about 50%, or about 10% to about 40%, or about 20% to about 30%. Thus, in some examples, the frequency and pulse width of the pulses may be selected such that the electrical stimulation may have a duty cycle in a range of about 5% to about 50%, where the frequency is selected to be in a range of about 1 Hz to about 1400 Hz (e.g., less than or equal to about 1000 Hz) and the pulse width is selected to be in a range of about 0.1 ms to about 5 ms (e.g., about 0.1 ms to about 1 ms). In some examples, the amplitude of the pulses may be selected to provide therapeutic efficacy and so that the intensity of the delivered electrical stimulation is less than or equal to one or both of a paresthesia threshold or perception threshold of the patient.

In some examples, the system may generate and deliver each of a plurality of electrical stimulation pulses before the system delivers one or more recharge pulses. The one or more recharge pulses may function to return the tissue of the patient to a relatively neutral charge subsequent to the delivery of the respective electrical stimulation pulse. For example, before an electrical stimulation pulse is delivered to tissue of a patient, the tissue near electrodes may have a relatively neutral charge. After the plurality of electrical stimulation pulses are generated and delivered, the tissue affected by the electrical stimulation pulses may hold a relatively positive or negative electrical charge (e.g., positive or negative as compared to the first relatively neutral charge and based on whether the tissue was close to the anode or cathode). The patient may receive therapy from this electrical charge on the tissue for some period of time, but prolonged charge maintained in tissue may damage tissue and/or affect the interface between the electrode and tissue. After the one or more recharge pulses are delivered to the tissue, the tissue may be returned to a charge near the first relatively neutral charge (e.g. no positive or negative electrical charge or approximately zero electrical charge remaining in the tissue). A charge that is near zero or approximately zero may be close enough to zero that the tissue will not be negatively affected by the small remaining electrical charge.

The one or more recharge pulses may generally be of an opposite polarity or amplitude of the respective electrical stimulation pulse(s) in order to neutralize the respective electrical stimulation pulse. In this way, a medical device can deliver a series of pseudo-continuous electrical stimulation pulses to a particular portion of tissue over a period of time of hours or days (with recharge signals delivered between some of the series of pseudo-continuous electrical stimulation pulses) without that portion of tissue becoming more electrically charged over that period of time. In some examples, the system may deliver a respective recharge signal for each respective electrical stimulation pulse. In other examples, the system may deliver fewer recharge pulses than the number of previously delivered stimulation pulses, such as one recharge pulse for a plurality of electrical stimulation pulses. In other examples, each electrical stimulation pulse is eventually followed with a respective recharge pulse. In examples where each electrical stimulation pulse is eventually followed with a respective recharge pulse, the system may deliver respective recharge pulses at the same time or at different times. For example, the respective recharge pulses may be delivered in the same order or a different order than the order in which the respective electrical stimulation pulses were delivered. In certain examples, the one or more recharge pulses may be withheld (e.g., purposefully delayed) for a period of time subsequent to when the final electrical stimulation pulse is generated and delivered. In other words, there may be a period of time between stimulation pulses and recharge pulses during which no stimulation pulses or recharge pulses are delivered by the system.

Due at least in part to a relatively high number of pulses delivered per unit of time without a recharge pulse and the selected pulse width, the dose (e.g., charge per second delivered) of the electrical stimulation signal may be high enough to elicit a therapeutic response from the patient, even though each individual pulse may have a relatively low amplitude. The relatively low amplitude of the pulses may also help keep the stimulation intensity level less than a perception or paresthesia threshold intensity level for the patient. In some examples, the plurality of pulses may have a duty cycle in a range of about 5% to about 50% and a frequency less than or equal to about 1000 Hz, and each of the pulses may have a pulse width in a range of about 0.1 ms to about 5 ms, such as about 0.1 ms to about 1 ms, or about 500 µs to about 1 ms. For example, the plurality of pulses may have a duty cycle in a range of about 5% to about 50% and a frequency less equal to about 1000 Hz, and each of the pulses may have a pulse width less than or equal to about 0.5 ms.

In some examples in which the high duty cycle, relatively low stimulation intensity electrical stimulation is delivered to a tissue site in a patient proximate to the spinal cord with a plurality of pulses delivered before one or more recharge pulses are delivered, the electrical stimulation may modulate nerve fibers and produce pain relief via mechanisms that do not rely on the activation of dorsal column fibers. Although the electrical stimulation may or may not also activate dorsal column fibers, the electrical stimulation may not rely on activation of dorsal column fibers, which may cause paresthesia, to provide therapeutic efficacy for pain or another patient condition. For example, the high duty cycle electrical stimulation may block endogenous action potentials in A-beta fibers at their branch points. A-beta fibers may be involved in some forms of chronic pain modulation, and the high duty cycle electrical stimulation may prevent A-fiber information from reaching the dorsal horn. Activation of dorsal column axons may cause paresthesia. Thus, the pain relief from the high duty cycle electrical stimulation described herein using relatively low amplitude pulses may be substantially paresthesia-free in some examples and with some patients. The paresthesia free electrical stimulation may be referred to as subliminal stimulation in some examples.

In some cases, the high duty cycle electrical stimulation described herein may modulate dural fibers, which may also be responsible for some aspects of pain (e.g., back pain) without causing activation of dorsal column fibers.

The mechanisms by which the high duty cycle, relatively low stimulation intensity electrical stimulation wherein a plurality of pulses is delivered before one or more recharge pulses are delivered as described herein may cause pain relief may include inhibition of spinal neurons, modulation of the activity of the central nervous system (CNS) and/or brainstem, or descending inhibition (e.g., suppression of pain messages to the brain).

The high duty cycle electrical stimulation techniques described herein may activate neurons in a different way than burst electrical stimulation techniques. In contrast to burst electrical stimulation techniques, the high duty cycle electrical stimulation described herein may provide better targeting of target tissue sites. For a given electrical stimulation dose (e.g., energy per second), burst electrical stimulation techniques may result in activation of more neural tissue (e.g., a larger volume of tissue) than the electrical stimulation described herein, which provides electrical stimulation with a higher frequency to achieve a dose sufficient to elicit a therapeutic response from a patient.

For example, the high duty cycle electrical stimulation described herein may deliver pulses having higher amplitudes, shorter pulse widths, or both higher amplitudes and shorter pulse widths than the burst electrical stimulation techniques. Compared to burst electrical stimulation techniques, the higher duty cycle described herein may allow for a larger therapeutic window for the amplitude of electrical stimulation (e.g., a range of values of the stimulation signal amplitude that provides efficacious electrical stimulation therapy), which may result in more freedom to titrate the amplitude of the pulses. The larger therapeutic window may help a clinician tailor the electrical stimulation to a particular patient to allow for different neural mechanisms to be activated in order to elicit a therapeutic response from the patient, e.g., while maintaining the intensity of the electrical stimulation below a threshold stimulation intensity level. In addition, the larger therapeutic window for the amplitude may provide a clinician with more freedom to select therapy parameter values that balance power efficiency (power consumed by the IMD when generating the electrical stimulation) with the therapeutic effect. Also, delivering a plurality of electrical stimulation pulses before delivering one or more recharge pulses for the plurality of electrical stimulation pulses may allow the system to build up charge in a certain portion of the tissue.

In some examples, a therapeutic window is defined as the values of an electrical stimulation parameter between an efficacy threshold, which may be the lowest electrical stimulation parameter value (or highest, depending on the parameter) at which efficacious effects of the electrical stimulation were first observed, and an adverse-effects threshold, which may be the lowest electrical stimulation parameter value (or highest, depending on the parameter) at which adverse effects of the electrical stimulation were first observed.

The high duty cycle electrical stimulation described herein may also provide better targeting of target tissue sites compared to high frequency electrical stimulation techniques, in which a plurality of pulses is delivered at frequencies greater than or equal to 1.5 kilohertz (kHz), For a given dose, the high frequency electrical stimulation techniques may result in activation of more neural tissue than the high duty cycle electrical stimulation described herein (e.g., a plurality of electrical stimulation pulses followed by one or more recharge signals for the plurality of electrical stimulation pulses), which provides electrical stimulation with wider pulse widths, but at lower frequencies than the high frequency electrical stimulation techniques to achieve a dose sufficient to elicit a therapeutic response from a patient. Compared to high frequency electrical stimulation techniques, the lower frequency of the high duty cycle electrical stimulation described herein may allow for a larger therapeutic window for the amplitude of electrical stimulation. As discussed above, a larger therapeutic window may help a clinician tailor the electrical stimulation to a particular patient and may provide the clinician with more freedom to select therapy parameter values that balance power efficiency with the therapeutic effect.

FIG. 1 is a conceptual diagram illustrating example system 10 that includes an implantable medical device (IMD) 14 configured to deliver electrical stimulation therapy to patient 12. In the example shown in FIG. 1, IMD 14 is configured to deliver SCS therapy. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 10 includes an IMD 14, leads 16A, 16B, and external programmer 18 shown in conjunction with a patient 12, who is ordinarily a human patient. In the example of FIG. 1, IMD 14 is an implantable electrical stimulator that is configured to generate and deliver electrical stimulation therapy to patient 12 via electrodes of leads 16A, 16B, e.g., for relief of chronic pain or other symptoms. IMD 14 may be a chronic electrical stimulator that remains implanted within patient 12 for weeks, months, or even years. In other examples, IMD 14 may be a temporary, or trial, stimulator used to screen or evaluate the efficacy of electrical stimulation for chronic therapy.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 14 may be implanted within other suitable sites within patient 12, which may depend, for example, on the target site within patient 12 for the delivery of electrical stimulation therapy. The outer housing of IMD 14 may be configured to provide a hermetic seal for components, such as rechargeable power source 18. In addition, in some examples, the outer housing of IMD 14 may be selected of a material that facilitates receiving energy to charge rechargeable power source 18.

Electrical stimulation energy, which may be constant current or constant voltage based pulses, for example, is delivered from IMD 14 to one or more target tissue sites of patient 12 via one or more electrodes (not shown) of implantable leads 16A and 16B (collectively "leads 16"). In the example of FIG. 1, leads 16 carry electrodes that are placed adjacent to the target tissue of spinal cord 20. One or more of the electrodes may be disposed at a distal tip of a lead 16 and/or at other positions at intermediate points along the lead. Leads 16 may be implanted and coupled to IMD 14. The electrodes may transfer electrical stimulation generated by an electrical stimulation generator (e.g., electrical generating circuitry) in IMD 14 to tissue of patient 12. Although leads 16 may each be a single lead, lead 16 may include a lead extension or other segments that may aid in implantation or positioning of lead 16. In some other examples, IMD 14 may be a leadless stimulator with one or more arrays of electrodes arranged on a housing of the stimulator rather than leads that extend from the housing. In addition, in some other examples, system 10 may include one lead or more than two leads, each coupled to IMD 14 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of lead 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

The therapy parameters for a therapy program (also referred to herein as a set of electrical stimulation parameter values) that controls delivery of stimulation therapy by IMD 14 through the electrodes of leads 16 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as rate or the like in the case IMD 14 is also configured for drug delivery.

Although FIG. 1 is directed to SCS therapy, e.g., used to treat pain, in other examples system 10 may be configured to treat any other condition that may benefit from electrical stimulation therapy. For example, system 10 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 12.

In some examples, lead 16 may include one or more sensors configured to allow IMD 14 to monitor one or more parameters of patient 12. The one or more sensors may be provided in addition to, or in place of, therapy delivery by lead 16.

IMD 14 is configured to deliver high dose electrical stimulation therapy to patient 12 via selected combinations of electrodes carried by one or both of leads 16, alone or in combination with an electrode carried by or defined by an outer housing of TMD 14. The target tissue for the high dose electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 20, such as within an intrathecal space or epidural space of spinal cord 20, or, in some examples, adjacent nerves that branch off of spinal cord 20. Leads 16 may be introduced into spinal cord 18 in via any suitable region, such as the thoracic, cervical or lumbar regions. Stimulation of spinal cord 18 may, for example, prevent pain signals from traveling through spinal cord 20 and to the brain of patient 12. Patient 12 may perceive the interruption of pain signals as a reduction in pain and, therefore, efficacious therapy results.

IMD 14 generates and delivers electrical stimulation therapy to a target stimulation site within patient 12 via the electrodes of leads 16 to patient 12 according to one or more therapy programs. A therapy program defines values for one or more parameters that define an aspect of the therapy delivered by IMD 14 according to that program. For example, a therapy program that controls delivery of stimulation by IMD 14 in the form of pulses may define values for voltage or current pulse amplitude, pulse width, recharge pulse withholding, and pulse rate for stimulation pulses delivered by IMD 14 according to that program.

Moreover, in some examples, IMD 14 delivers electrical stimulation therapy to patient 12 according to multiple therapy programs, which may be stored as a therapy program group. For example, as described below, in some examples, IMD 14 may deliver different pulses of a high duty cycle electrical stimulation signal via respective electrode combinations, and each of the electrode combinations may be associated with a respective therapy program. The therapy programs may be stored as a group, such that when IMD 14 generates and delivers electrical stimulation therapy via a selected group, IMD 14 delivers high duty cycle electrical stimulation signal via two or more therapy programs.

IMD 14 is configured to deliver a recharge signal (e.g., one or more recharge pulses or other waveforms), which may help balance a charge accumulation that may occur within tissue proximate the electrodes used to deliver the electrical stimulation. The recharge signal may also be referred to as a "recharge pulse" or a "recovery signal" or a "charge balancing signal" and may have a polarity opposite to that of the electrical stimulation signal generated and delivered by IMD 14. While recharge pulses are primarily referred to herein, in other examples, a recharge signal can have any suitable waveform.

In some examples, IMD 14 may deliver one or more recharge signals after delivery of multiple pulses of a high duty electrical stimulation signal, which may be defined by one therapy program or by multiple therapy programs. Thus, rather than charge balancing on a pulse-by-pulse basis (e.g., delivering one recharge pulse after each electrical stimulation pulse), in some examples, IMD 14 delivers one or more recharge pulses after delivery of two or more electrical stimulation pulses. In some examples, IMD 14 delivers a high duty electrical stimulation signal to patient 12 according to multiple therapy programs by at least interleaving pulses of two or more therapy programs, the pulses having a first polarity. In some of these examples, IMD 14 may wait to deliver one or more recharge pulses until after one or more pulses of each of the therapy programs are delivered, the one or more recharge pulses having a second polarity opposite to the first polarity. In some examples, each recharge pulse relates to (e.g., negate the accumulated charge of) a single pulse, while in other examples a single recharge pulse may relate to (e.g., negate the accumulated charge of) a plurality of electrical pulses. Thus, in some examples, IMD 14 may not deliver any recharge signals between therapy programs, but, rather, may withhold the delivery of one or more recharge signals until after IMD 14 delivers a plurality of pulses according to two or more therapy programs.

In some examples, IMD 14 is configured to generate and deliver high duty cycle electrical stimulation therapy to patient 12 via two or more electrodes, e.g., of leads 16 and/or a housing of IMD 14. In some examples, the high duty cycle electrical stimulation signal may have a duty cycle in a range of about 5% to about 50%, a frequency in a range of about 1 Hz to about 1400 Hz (e.g., less than about 1000 Hz in some examples), and a pulse width less than or equal to about 5 ms, such as about 0.1 ms to about 5 ms, or about 0.1 ms to about 1 ms. The amplitude and pulse width of the electrical stimulation signal are selected such that a stimulation intensity level of the electrical stimulation signal is less than a perception or paresthesia threshold intensity level for patient 12. For example, the amplitude may be selected to be in a range of about 1 mA to about 25 mA, such as in a range of about 1 mA to about 5 mA.

In some examples, IMD 14 delivers the pulses of the high duty cycle electrical stimulation signal via different electrode combinations. For example, IMD 14 may alternate delivery of pulses between two different electrode combinations, or may otherwise interleave the pulses using two or more electrode combinations in any suitable order. Regardless of the number of electrode combinations with which IMD 14 delivers the pulses, however, the combination of pulses delivered over time define an electrical stimulation signal that may have a duty cycle in a range of about 5% to about 50% and a frequency in a range of about 1 Hz to about 1400 Hz.

A user, such as a clinician or patient 12, may interact with a user interface of an external programmer 18 to program IMD 14. Programming of IMD 14 may refer generally to the generation and transfer of commands, programs, or other information to control the operation of IMD 14. In this manner, IMD 14 may receive the transferred commands and programs from programmer 18 to control stimulation therapy. For example, external programmer 18 may transmit therapy programs, stimulation parameter adjustments, therapy program selections, therapy program group selections, user input, or other information to control the operation of IMD 14, e.g., by wireless telemetry or wired connection.

In some cases, external programmer 18 may be characterized as a physician or clinician programmer if it is primarily intended for use by a physician or clinician. In other cases, external programmer 18 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy. In general, a physician or clinician programmer may support selection and generation of programs by a clinician for use by IMD 14, whereas a patient programmer may support adjustment and selection of such programs by a patient during ordinary use. In other examples, external programmer 18 may be included, or part of, an external charging device that recharges a power source of IMD 14. In this manner, a user may program and charge IMD 14 using one device, or multiple devices.

As described herein, information may be transmitted between external programmer 18 and IMD 14. Therefore, IMD 14 and programmer 18 may communicate via wireless communication using any techniques known in the art. Examples of communication techniques may include, for example, radiofrequency (RF) telemetry and inductive coupling, but other techniques are also contemplated. In some examples, programmer 18 may include a communication head that may be placed proximate to the patient's body near the IMD 14 implant site in order to improve the quality or security of communication between IMD 14 and programmer 18. Communication between programmer 18 and IMD 14 may occur during power transmission or separate from power transmission.

Although IMD 14 is generally described herein, techniques of this disclosure may also be applicable to external or partially external medical device in other examples. For example, IMD 14 may instead be configured as an external medical device coupled to one or more percutaneous medical leads. The external medical device may be a chronic, temporary, or trial electrical stimulator. In addition, an external electrical stimulator may be used in addition to one or more IMDs 14 to deliver electrical stimulation described herein.

Figure 2:
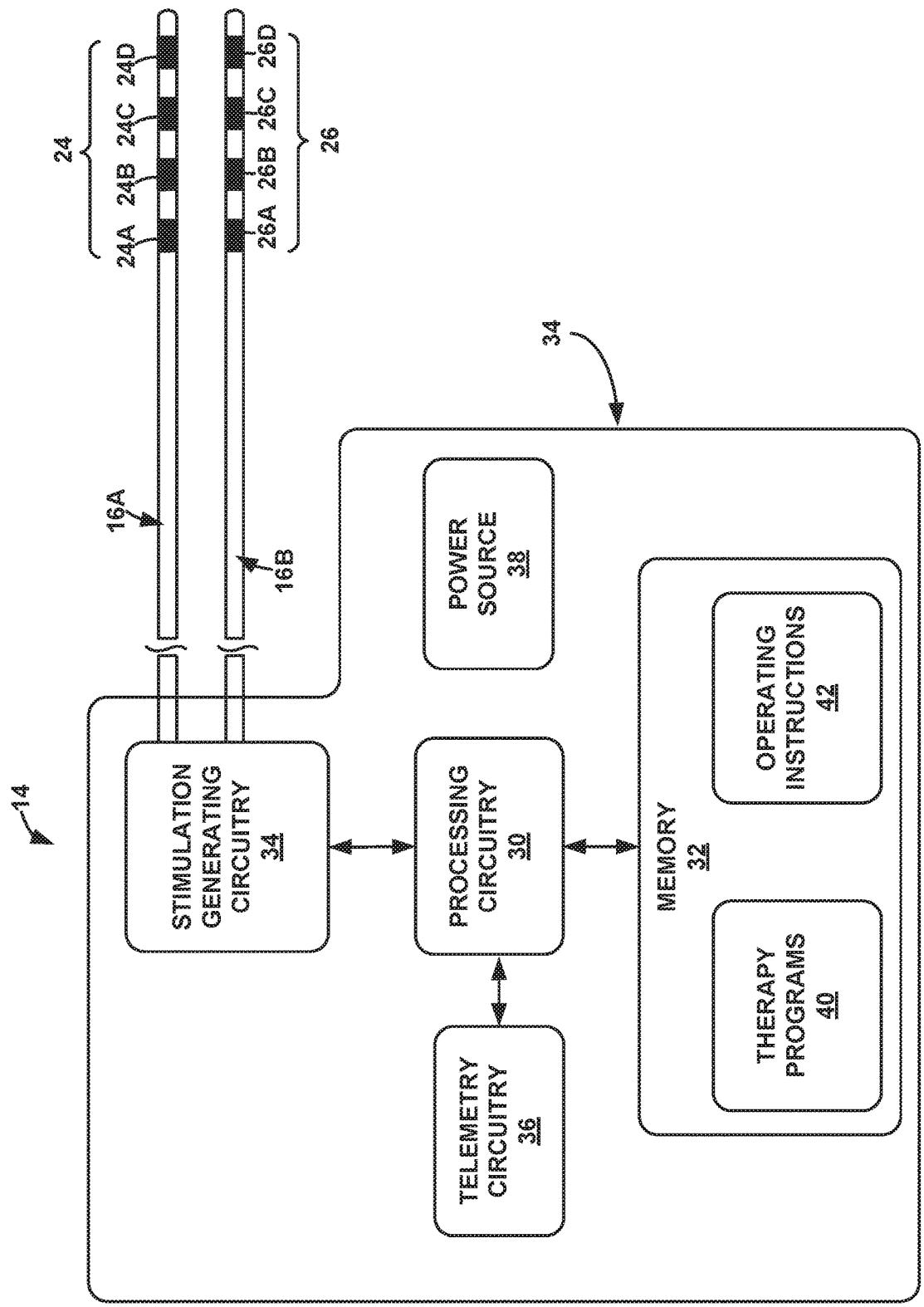
FIG. 2 is a block diagram of the example IMD of FIG. 1.

FIG. 2 is a functional block diagram illustrating various components of an example IMD 14. In the example shown in FIG. 2, IMD 14 includes processing circuitry 30, memory 32, stimulation generating circuitry 34, telemetry circuitry 36, and power source 38. In other examples, IMD 14 may include a greater or fewer number of components. For example, IMD 14 may also include sensing circuity configured to sense one or more patient parameters, an inductive coil to receive power from an external charging device, and recharge circuitry that manages recharging of power source 38.

Processing circuitry 30 is operably connected to and configured to access information from memory 32 and to control stimulation generating circuitry 34 and telemetry circuit 36. Components described as processing circuitry 30 and other processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. In general, IMD 14 may comprise any suitable arrangement of hardware, alone or in combination with software and/or firmware, to perform the various techniques described herein attributed to IMD 14 and processing circuitry 30. In various examples, IMD 14 may include one or more components as part of processing circuitry 30, such as one or more DSPs, ASICs, FPGAs, programmable logic circuitry, or the like, either alone or in any suitable combination.

Memory 32 may store therapy programs 40 (or other instructions that specify therapy parameter values for the therapy provided by stimulation generating circuitry 34 and IMD 14), operating instructions 42 for execution by processing circuitry 30, and any other information regarding therapy of patient 12. In some examples, memory 32 may also store instructions for communication between IMD 14 and programmer 18, or any other instructions required to perform tasks attributed to IMD 14. Memory 32 may include separate memories for storing therapy programs, operating instructions, and any other data that may benefit from separate physical memory components.

Memory 32 may be, for example, random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Although processing circuitry 30, stimulation generating circuitry 34, and telemetry circuitry 36 are described as separate components, in some examples, processing circuitry 30, 34, and telemetry circuitry 36 may be functionally integrated. In some examples, processing circuitry 30, stimulation generating circuitry 34, and telemetry circuitry 36 may correspond to individual hardware units, such as ASICs, DSPs, FPGAs, or other hardware units.

Stimulation generating circuitry 34 forms a therapy delivery component of IMD 14. Processing circuitry 30 controls stimulation generating circuitry 34 to generate and deliver electrical stimulation via electrode combinations formed by a selected subset of electrodes 24A-24D, 26A-26D (collectively, "electrodes 24, 26") of leads 16. Stimulation generating circuitry 34 may deliver electrical stimulation therapy via electrodes on one or more of leads 16, e.g., as stimulation pulses. Stimulation generating circuitry 34 may include stimulation generation circuitry to generate stimulation pulses and, in some examples, switching circuitry to switch the stimulation across different electrode combinations, e.g., in response to control by processing circuitry 30. In other examples, stimulation generating circuitry 34 may include multiple current sources to drive more than one electrode combination at one time.

In some examples, processing circuitry 30 controls stimulation generating circuitry 34 by accessing memory 32 to selectively access and load at least one of the therapy programs 40 to stimulation generating circuitry 34. The stimulation parameter values of the stored therapy programs 40 may include, for example, a voltage amplitude, a current amplitude, a pulse frequency, a pulse width, a duty cycle, and a subset of electrodes 24, 26 of leads 16 for delivering the electrical stimulation signal. An electrode configuration may include the one or more electrodes 24, 26 with which stimulation generating circuitry 34 delivers the electrical stimulation to tissue of a patient, and the associated electrode polarities.

In some examples, IMD 14 may deliver a high duty cycle electrical stimulation signal to a target tissue site within patient 12 via one electrode combination, such that all pulses are delivered via the same electrode combination. In other examples, IMD 14 may deliver a high duty cycle electrical stimulation signal to a target tissue site within patient 12 via two or more electrode combinations, such that IMD 14 delivers at least two different pulses of a high duty cycle electrical stimulation signal via respective electrode combinations. The delivery of different pulses via respective electrode combinations may help target the electrical stimulation to a target tissue site (e.g., in the case of pain relief, the target may be towards a midline of spinal cord 20, for example, near the T9-T10 vertebrae). The electrical stimulation delivered by each electrode combination, which may be referred to as a sub-signal, may be interleaved (e.g., delivered at different times) to define the high duty cycle electrical stimulation signal. In some of these examples, each sub-signal is associated with a respective therapy program. Thus, processing circuitry 30 may control stimulation generating circuitry 34 to generate and deliver a high duty cycle electrical stimulation signal by at least accessing memory 32 to selectively access and load multiple therapy programs 40 to stimulation generating circuitry 34.

IMD 14 also includes components to receive power from programmer 18 or a separate charging device to recharge a battery of power source 38. Power source 38 may include one or more capacitors, batteries, or other energy storage devices. IMD 14 may thus also include an inductive coil and recharge circuitry (both not shown) configured to manage the recharging session for power source 38. Although inductive coupling may be used to recharge power source 38, other wireless energy transfer techniques may alternatively be used. Alternatively, power source 38 may not be rechargeable. In some examples, the power source 38 of IMD 14 may include a plurality of current sources in which each current source is capable of generating pulses, such that numerous electrical stimulation pulses may be delivered simultaneously to the patient 12.

Processing circuitry 30 may also control the exchange of information with programmer 18 and/or an external programmer using telemetry circuitry 36. Telemetry circuitry 36 may be configured for wireless communication using RF protocols, inductive communication protocols, or any other suitable technique. To support the wireless communication, telemetry circuit 36 may include appropriate electronic components, such as amplifiers, filters, mixers, encoders, decoders, and the like. Processing circuitry 30 may transmit operational information and receive therapy programs or therapy parameter adjustments via telemetry circuitry 36. Also, in some examples, IMD 14 may communicate with other implanted devices, such as stimulators, control devices, or sensors, via telemetry circuitry 36.

Figure 3:
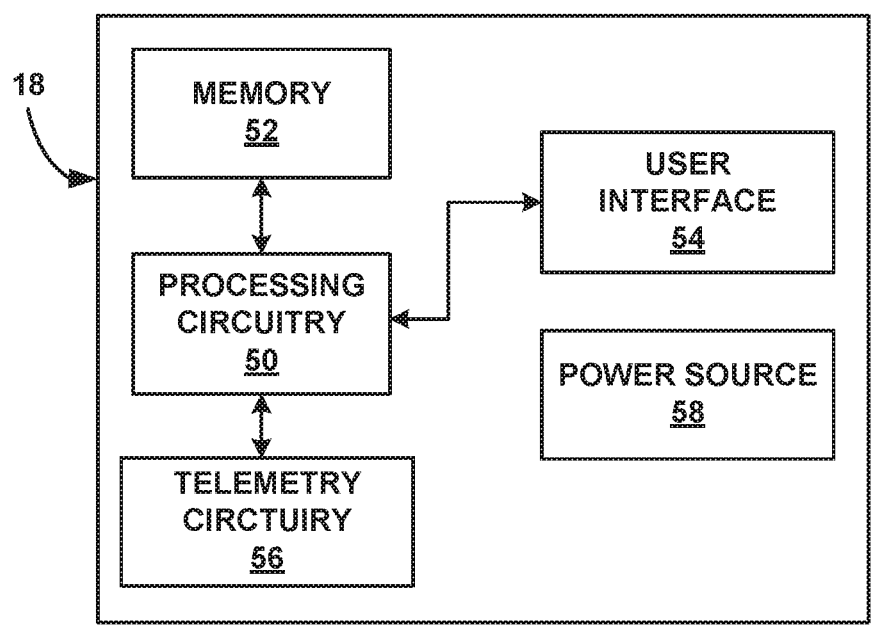
FIG. 3 is a block diagram of the example external programmer of FIG. 1.

FIG. 3 is a block diagram of an example external programmer 18. While programmer 18 may generally be described as a hand-held device, programmer 18 may be a larger portable device or a more stationary device in some examples. In addition, in other examples, programmer 18 may be included as part of an external charging device or include the functionality of an external charging device. As illustrated in FIG. 3, programmer 18 may include processing circuitry 50, memory 52, user interface 54, telemetry circuitry 56, and power source 58. Memory 52 may store instructions that, when executed by processing circuitry 50, cause processing circuitry 50 and external programmer 18 to provide the functionality ascribed to external programmer 18 throughout this disclosure.

Programmer 18 comprises any suitable arrangement of hardware, alone or in combination with software and/or firmware, to perform the techniques attributed to programmer 18, and processing circuitry 50, user interface 54, and telemetry circuitry 56 of programmer 18. In various examples, processing circuitry 50 may include one or more processors, such as one or more microprocessors, DSPs, ASICs, FPGAs, or any other equivalent integrated or discrete logic circuitry, as well as any combinations of such components. Programmer 18 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processing circuitry 50 and telemetry circuitry 56 are described as separate electrical circuitry components, in some examples, processing circuitry 50 and telemetry circuitry 56 are functionally integrated. In some examples, processing circuitry 50 and telemetry circuitry 56 correspond to individual hardware units, such as ASICs, DSPs, FPGAs, or other hardware units.

Memory 52 may store instructions that, when executed by processing circuitry 50, cause processing circuitry 50 and programmer 18 to provide the functionality ascribed to programmer 18 throughout this disclosure. In addition, in some examples, memory 52 stores one or more therapy programs for execution by IMD 14 to deliver high dose electrical stimulation therapy.

User interface 54 may include a button or keypad, lights, a speaker for voice commands, a display, such as a liquid crystal (LCD), light-emitting diode (LED), or organic light-emitting diode (OLED). In some examples the display may be a touch screen. User interface 54 may be configured to display any information related to the delivery of stimulation therapy, such as currently selected parameter values, intensity thresholds, or any other therapy information. User interface 54 may also receive user input via user interface 54. The input may be, for example, in the form of pressing a button on a keypad or selecting an icon from a touch screen. The input may request starting or stopping electrical stimulation, or requesting some other change to the delivery of electrical stimulation.

Telemetry circuitry 56 may support wireless communication between IMD 14 and programmer 18 under the control of processing circuitry 50. Telemetry circuitry 56 may also be configured to communicate with another computing device via wireless communication techniques, or direct communication through a wired connection. In some examples, telemetry circuitry 56 may be substantially similar to telemetry circuitry 36 of IMD 14 described herein, providing wireless communication via an RF or proximal inductive medium. In some examples, telemetry circuitry 56 may include an antenna, which may take on a variety of forms, such as an internal or external antenna.

Examples of local wireless communication techniques that may be employed to facilitate communication between programmer 18 and IMD 14 include RE communication according to the 802.11 or Bluetooth specification sets or other standard or proprietary telemetry protocols. In this manner, other external devices may be capable of communicating with programmer 18 without needing to establish a secure wireless connection.

Figure 4:
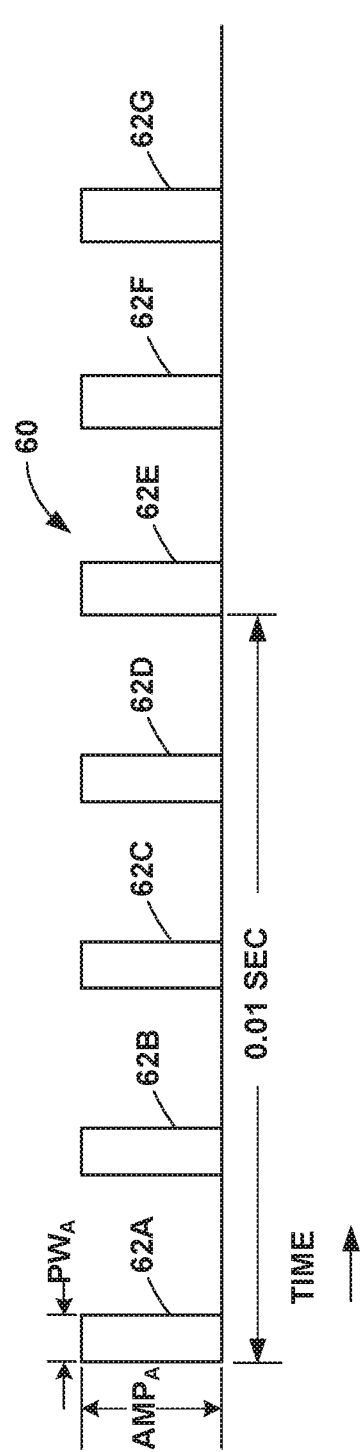
FIGS. 4 and 5 illustrate an example of high duty cycle electrical stimulation waveforms.

FIG. 4 is a timing diagram of an example high density electrical stimulation signal 60 that IMD 14 may generate and deliver to patient 12. Electrical stimulation signal 60 includes a plurality of pulses 62A-62G (collectively, "pulses 62"). Although seven pulses are shown in FIG. 4, stimulation signal 60 may include any number of pulses, which may depend on the time period over which IMD 14 delivers stimulation signal 60 to patient 12. Each pulse 62 has an amplitude $AMP_A$ and a pulse width $PW_A$. In some examples, each pulse 62 of electrical stimulation signal 60 can have the same amplitude $AMP_A$ and pulse width $PW_A$. In other examples, at least one pulse 62 of signal 60 may have a different amplitude $AMP_A$ and/or pulse width $PW_A$ than another pulse 62. However, in either example, electrical stimulation signal 60 has a duty cycle of about 5% to about 50% and a frequency in a range of about 1 Hz to about 1400 Hz or less (e.g., less than or equal to about 1000 Hz). In addition, in some examples, each pulse 62 may have a pulse width $PW_A$ in a range of about 0.1 ms to about 5 ms (e.g., less than or equal to about 1 ms, such as in a range of about 0.5 ms to about 1 ms).

The duty cycle of electrical stimulation signal 60, which may be the on-time of electrical stimulation signal 60 per unit of time (e.g., one second), can be characterized by a product of a frequency and a pulse width $PW_A$ of pulses 62. For example, for a stimulation signal 60 having a frequency of about 800 Hz and a pulse width of about 300 microseconds (µs) (0.0003 seconds), stimulation signal 60 may have a duty cycle of about 24%, calculated as follows:

$$\text{Duty Cycle} = \frac{800 \text{ pulses}}{1 \text{ sec}} * \frac{0.0003 \text{ sec}}{1 \text{ pulse}} = \qquad \text{(Equation 1)}$$

$$\frac{0.24 \text{ sec therapy "on time"}}{1 \text{ sec total time}} = 24\%$$

As another example, for a stimulation signal having a frequency of about 300 Hz and a pulse width of about 700 µs, stimulation signal 60 may have a duty cycle of about 21%, calculated as follows:

$$\text{Duty Cycle} = \frac{300 \text{ pulses}}{1 \text{ sec}} * \frac{0.0007 \text{ sec}}{1 \text{ pulse}} = \qquad \text{(Equation 2)}$$

$$\frac{0.21 \text{ sec therapy "on time"}}{1 \text{ sec total time}} = 21\%$$

In some examples, for a frequency of less than or equal to about 1000 Hz, the pulse width $PW_A$ of pulses 62 can be selected such that stimulation signal 60 has a duty cycle of about 20% to about 50%. In addition, the amplitude $AMP_A$ of stimulation signal 60 can be selected such that the dose of electrical stimulation signal 60 (having the desired duty cycle) is sufficient to elicit a therapeutic response from patient 12 when IMD 14 delivers electrical stimulation signal 60 to a target tissue site in patient 12 (e.g., proximate spinal cord 20, a peripheral nerve, a muscle, or another suitable tissue site, which may be selected based on the patient condition being treated). For example, in examples in which pulses 62 are substantially similar (e.g., identical or nearly identical amplitudes $AMP_A$ and pulse widths $PW_A$), the dose of electrical stimulation signal 60 can be determined to be a product of the amplitude $AMP_A$ and pulse width $PW_A$ of the pulses 62A-62D, which are the pulses 62 delivered over a one second period of time. In some examples in which IMD 14 delivers stimulation signal 60 to patient 12 to spinal cord 20 to treat pain, stimulation signal 60 may have a duty cycle of about 20% to about 50%, a frequency in a range of about 1 Hz to about 1400 Hz, and pulses 62 may each have a pulse width $PW_A$ less in a range of about 0.1 ms to about 5 ms and an amplitude $AMP_A$ below a paresthesia threshold of patient 12.

Stimulation generating circuitry 34 of IMD 14 may generate and deliver high duty cycle electrical stimulation signal 60 using any suitable technique. In some examples, stimulation generating circuitry 34 may deliver each of the pulses 62 with the same electrode combination. In some examples, stimulation generating circuitry 34 may deliver one or more recharge pulses (also referred to as a "recovery pulse" or a "charge balancing pulse") after a predetermined number of pulses 62 are delivered, the predetermined number being greater than one. Thus, rather than charge balancing on a pulse-by-pulse basis (e.g., delivering one recharge pulse after each pulse 62), in some examples, processing circuitry 30 may control stimulation generating circuitry 34 to deliver one or more recharge pulses after delivery of two or more pulses 62. In other examples, processing circuitry 30 may control stimulation generating circuitry 34 to deliver pulses to promote charge balance on a pulse-by-pulse basis.

In other examples, stimulation generating circuitry 34 may deliver different pulses 62 via respective electrode combinations, such that the high pulse density electrical stimulation signal is delivered via multiple therapy programs. For example, under the control of processing circuitry 30, stimulation generating circuitry 34 may deliver pulses 62A, 62C, 62E, 62G with a first electrode combination, and deliver pulses 62B, 62D, 62F with a second, different electrode combination. In this example, pulses 62A, 62C, 62E, 62G can be part of a first sub-signal delivered via the first electrode combination, and pulses 62B, 62D, 62F can be part of a second sub-signal delivered via the second electrode combination. The first and second sub-signals, when delivered together over time such that the pulses of the sub-signals interleaved together as shown in FIG. 4, combine to define high duty cycle electrical stimulation signal 60. Although two sub-signals are used here as an example, in other examples, stimulation generating circuitry 34 of IMD 14 may generate and deliver high duty cycle electrical stimulation signal 60 using any suitable number of sub-signals. In some examples, stimulation generating circuitry 34 may generate each sub-signal using a respective therapy program, which may be stored as a group in memory 32 of IMD 14 (FIG. 2).

In some examples in which stimulation generating circuitry 34 may deliver different pulses 62 via different electrode combinations, processing circuitry 30 may control stimulation generating circuitry 34 may deliver one or more recharge pulses after a predetermined number of pulses 62 are delivered, the predetermined number being greater than one. The predetermined number of pulses 62 may include pulses generated according to different therapy programs. Thus, in some examples, stimulation generating circuitry 34 may deliver one or more recharge pulses after pulses of different sub-signals are delivered. For example, under the control of processing circuitry 30, stimulation generating circuitry 34 may deliver one or more recharge pulses after stimulation generating circuitry delivers pulses 62A and 62B, rather than delivering one or more recharge pulses between pulses 62A, 62B, and then again after pulse 62B, In this example, stimulation generating circuitry 34 may wait to deliver one or more recharge pulses until after stimulation generating circuitry delivers pulses 62C and 62D, rather than delivering one or more recharge pulses between pulses 62C, 62D, and then again after pulse 62B. In other examples, processing circuitry 30 may control stimulation generating circuitry 34 to deliver recharge pulses to balance charge on a pulse-by-pulse basis.

Stimulation generating circuitry 34 can deliver the sub-signals using electrodes from a single lead 16A or from two or more leads 16B. For example, under the control of processing circuitry 30, stimulation generating circuitry 34 may deliver a first pulse 62A with electrode 24A of lead 16A together with a housing electrode of outer housing 34 of IMD 14 and deliver pulse 62B with electrode 24B of lead 16A together with a housing electrode of outer housing 34. As another example, under the control of processing circuitry 30, stimulation generating circuitry 34 may deliver a first pulse 62A with electrodes 24A, 24B of lead 16A and deliver pulse 62B with electrodes 24B, 24C of the same lead 16A. In another example, stimulation generating circuitry 34 may deliver different pulses 62 with electrodes of different leads. Processing circuitry 30 may, for example, control stimulation generating circuitry 34 to alternate delivery of pulses 62 between leads 16A, 16B, or control stimulation generating circuitry 34 to otherwise deliver pulses 62 with electrodes of each lead 16A, 16B at different times. For example, under the control of processing circuitry 30, stimulation generating circuitry 34 may deliver a first pulse 62A with electrodes 24A, 24B of lead 16A and deliver pulse 62B with electrodes 26A, 26B of lead 16B.

Regardless of the number of electrode combinations with which stimulation generating circuitry 34 delivers pulses 62, the combination of pulses 62 may combine to define electrical stimulation signal 60 having a duty cycle in a range of about 20% to about 50% and a frequency in a range of about 1 Hz to about 1400 Hz.

Delivery of each sub-signal by stimulation generating circuitry 34 may generate a stimulation field within tissue of the patient, where the stimulation field may be a volume of tissue through which the electrical current from the delivered sub-signal propagates. The electrode combinations with which pulses 62 are delivered and the frequency of high duty cycle electrical stimulation signal 60 can be selected such that the combination of pulses 62A, 62B (or any other number of pulses 62 delivered from any suitable number of different electrode combinations) results in stimulation fields that overlap. The region of overlap of the stimulation fields may be configured to target neural areas responsive to the high duty cycle mechanisms described herein, e.g., to provide the desired therapeutic effect. In some examples, the regions of the stimulation fields that do not overlap may not provide any therapeutic effect.

In some examples, processing circuitry 30 controls stimulation generating circuitry 34 to generate and deliver pulses 62 via two or more therapy programs, each defining a respective electrode combination. For example, some pulses 62 may be part of a first sub-signal defined by a first therapy program and delivered by stimulation generating circuitry 34 via a first electrode combination, and other pulses 62 may be part of a second sub-signal defined by a second therapy program and delivered by stimulation generating circuitry 34 via a second electrode combination. Stimulation generating circuitry 34 may interleave delivery of pulses of the first and second sub-signals, such that the pulses only partially overlap in time or do not overlap in time. Delivery of the first and second sub-signals may generate respective stimulation fields within tissue. In some examples, the stimulation fields, individually and when overlapping, have stimulation intensities less than at least one of: a perception threshold or a paresthesia threshold of the patient. In addition, in some examples, each pulse of the first and second sub-signals has a pulse width less than or equal to about 5 milliseconds, and stimulation generating circuitry 34 may interleave delivery of pulses of the first and second sub-signals to deliver electrical stimulation pulses at a frequency in a range of about 1 Hz to about 1400 Hz. In some examples, processing circuitry 30 controls stimulation generating circuitry 34 to deliver a recharge signal following the delivery of at least one pulse of each of the first and second electrical sub-signals.

Delivering stimulation signal 60 as multiple sub-signals delivered via respective electrode combinations may help reduce the charge density at the electrode-tissue interface of particular electrodes. In addition, delivering stimulation signal 60 via multiple sub-signals may provide more flexibility in programming the electrical stimulation therapy that has an intensity below the perception or paresthesia threshold intensity level of patient 12 because the sub-signals may each have relatively low stimulation intensities, but due to the overlap in the stimulation fields that may result from the interleaving of the delivery of the sub-signals, the sub-signals may be combined to provide efficacious electrical stimulation therapy to patient 12.

In some examples in which stimulation generating circuitry 34 generates and delivers a plurality of sub-signals in order to deliver the electrical stimulation signal having the high duty cycle and frequency less than or equal to about 1400 Hz described herein, stimulation generating circuitry 34 may recharge at the end of the pulse train, e.g., after the pulses of the plurality of sub-signals are delivered. In other examples, stimulation generating circuitry 34 may recharge after each delivered pulse.

Figure 5:
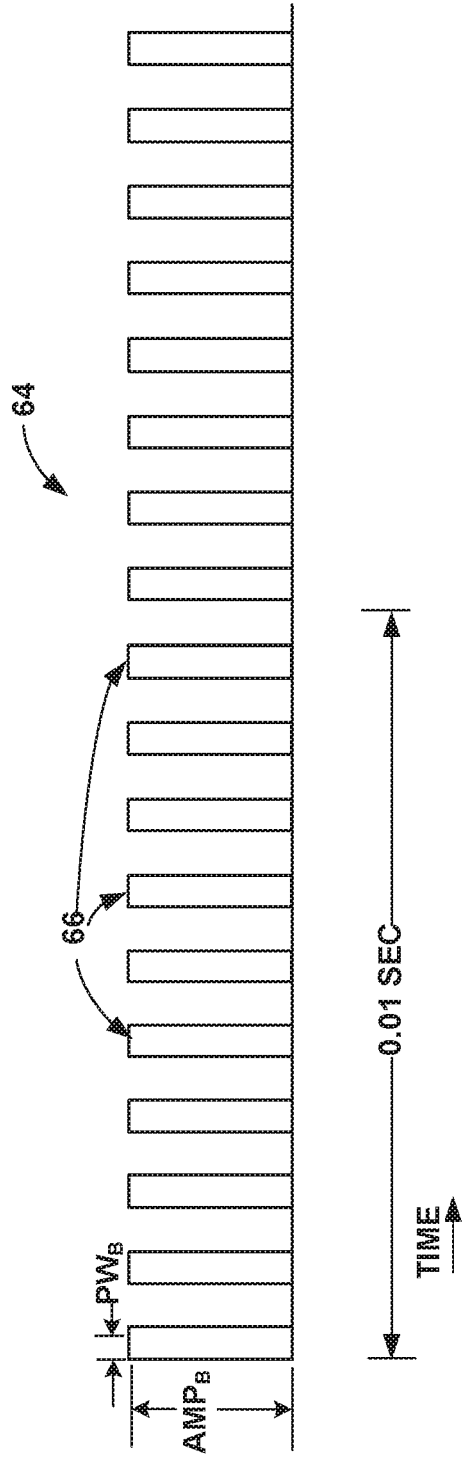

FIG. 5 is a timing diagram of another example high duty cycle electrical stimulation signal 64 that IMD 14 may generate and deliver to patient 12. Electrical stimulation signal 64 includes a plurality of pulses 66. Stimulation signal 64 may include any number of pulses 66, which may depend on the duration that IMD 14 delivers stimulation signal 64 to patient 12. As with stimulation signal 60 (FIG. 4), stimulation signal 64 may have duty cycle of about 5% to about 50%, a frequency in a range of about 1 Hz to about 1400 Hz. However, in contrast to stimulation signal 60, each pulse 66 of stimulation signal 64 has a smaller pulse width $PW_B$ and a higher amplitude $AMP_B$ than each of the pulses 62 of stimulation signal 60. The charge density of stimulation signal 64 may be similar to (e.g., identical or nearly identical) to stimulation signal 60, e.g., because the higher amplitude $AMP_B$ may compensate for the decrease in energy delivery resulting from the decrease in pulse width $PW_B$ relative to pulses 62 of signal 60. As with amplitude $AMP_A$, amplitude $AMP_B$ may be less than or equal to a paresthesia or perception threshold of patient 12. In addition, the duty cycle of signal 64 can be substantially the same as the duty cycle of signal 60 (FIG. 4), despite the smaller pulse width $PW_B$, due at least in part to the greater number of pulses 66 per second than signal 60.

Stimulation generating circuitry 34 of IMD 14 may generate and deliver high duty cycle electrical stimulation signal 64 using any suitable technique, such as those described with respect to signal 60.

As discussed above, due to potentially different mechanisms of action, a patient may respond differently to the high duty cycle electrical stimulation described herein, which may have a duty cycle of about 5% to about 50% and a frequency in a range of about 1 Hz to about 1400 Hz, compared to burst electrical stimulation techniques and high frequency electrical stimulation techniques.

FIG. 6 is a timing diagram of an example burst electrical stimulation signal 68, which includes a plurality of pulses 70A-70H (collectively, "pulses 70"). Burst electrical stimulation signal 68 has fewer pulses 70 per unit of time (e.g., one second) than high duty cycle electrical stimulation signals 60, 64 (FIGS. 4 and 5). During a particular period of time, e.g., one second as shown in FIG. 6, an IMD delivers a burst of pulses 70A-70D of electrical stimulation signal 68 for a first time period 72, which is immediately followed by a second period of time 74 during which the IMD does not deliver any electrical stimulation, but, rather, delivers one or more recovery pulses. Second time period 74 may be referred to as a "recovery period." After second time period 74, the IMD 14 may deliver another burst of pulses 70E-70H, which may be followed by another recovery period. First and second time periods 72, 74 may be substantially equal (e.g., equal or nearly equal) in some examples, and different in other examples.

In contrast to burst electrical stimulation signal 68, delivery of high duty cycle electrical stimulation signals 60, 64 by IMD 14 may provide better targeting of target tissue sites. For a given dose, burst electrical stimulation signal 68 may result in activation of more neural tissue (e.g., a larger volume of tissue) than high duty cycle electrical stimulation signals 60, 64, which may each provide electrical stimulation with a higher duty cycle than burst electrical stimulation signal 68 and with smaller pulse widths.

FIG. 7 is a timing diagram of an example high frequency electrical stimulation signal 76, which includes a plurality of pulses 78. High frequency electrical stimulation signal 76 has a higher frequency than high duty cycle electrical stimulation signals 60, 64 (FIGS. 4 and 5, such that signal 76 has a greater number of pulses 78 per unit of time than high duty cycle electrical stimulation signals 60, 64). For example, high frequency electrical stimulation signal 76 may have a frequency of 1500 Hz to about 100 kiloHz, or greater, whereas high duty cycle electrical stimulation signals 60, 64 may each have a frequency less than or equal to about 1400 Hz.

For a given duty cycle, high frequency electrical stimulation signal 76 may result in activation of more neural tissue than high duty cycle electrical stimulation signals 60, 64, which have pulses 62, 66, respectively, with higher pulse widths than pulses 78 of high frequency electrical stimulation signal 76. The lower frequency of high duty cycle electrical stimulation signals 60, 64 may allow for a larger therapeutic window for the pulse amplitudes $AMP_A$ and $AMP_A$, which may help a clinician tailor the electrical stimulation to a particular patient to allow for different neural mechanisms to be activated in order to elicit a therapeutic response from the patient. The therapeutic window for the pulse amplitudes $AMP_A$ and $AMP_A$ can be, for example, the range of amplitude values that provide efficacious therapy to patient 12 without resulting in undesired side effects.

Figure 8:
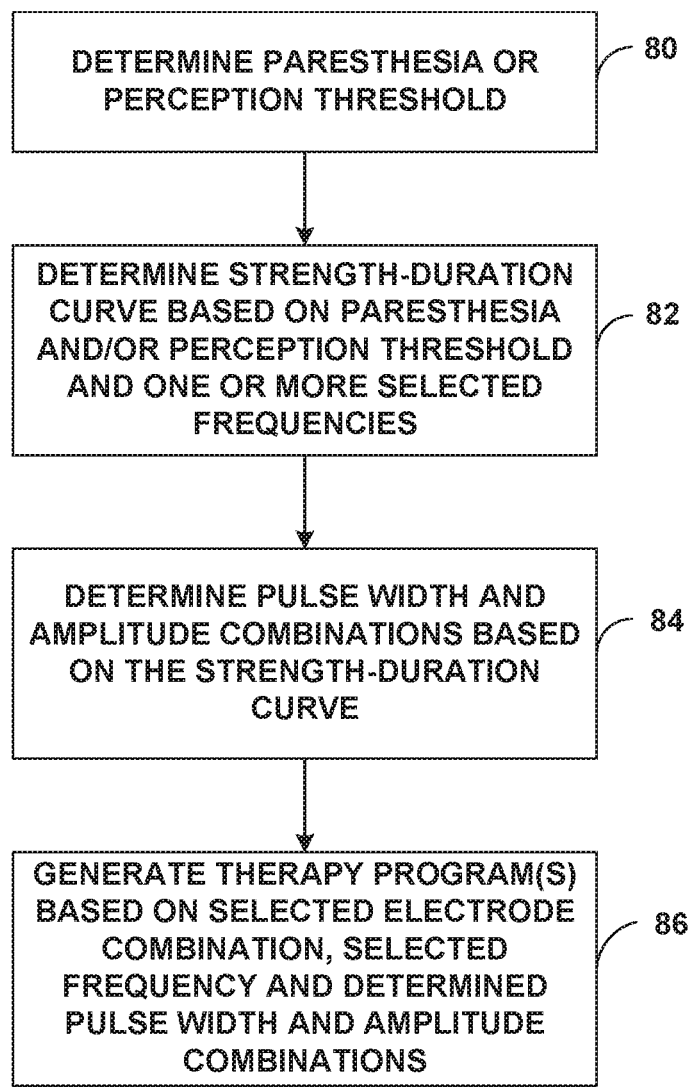
FIG. 8 is a flow diagram of an example method of programming high dose electrical stimulation therapy having a stimulation intensity level that is less than a perception or paresthesia threshold intensity level for a patient.

The electrical stimulation parameter values with which IMD 14 may generate and deliver the high density electrical stimulation described herein, having a duty cycle of about 5% and about 50%, a frequency less in a range of about 1 Hz to about 1400 Hz (e.g., less than or equal to about 1000 Hz), and a pulse width of about 5 ms or less, may be selected using any suitable technique. FIG. 8 is a flow diagram of an example technique for selecting the electrical stimulation parameter values. While FIG. 8 is described with respect to processing circuitry 30 of IMD 14, in other examples, processing circuitry 50 of programmer 18 may perform any part of the technique described with respect to FIG. 8, alone or in combination with processing circuitry 30 of IMD 14.

In the technique shown in FIG. 8, processing circuitry 30 determines a paresthesia or perception threshold intensity level for patient 12 (80), e.g., using the technique described below with respect to FIG. 9, by retrieving a stored paresthesia or perception threshold intensity level from memory 32 (FIG. 2), or by receiving a paresthesia or perception threshold intensity level from another device, e.g., programmer 18. Processing circuitry 30 may, for example, determine the paresthesia threshold (80), determine the perception threshold (80), determine the lower of the paresthesia threshold intensity level or the perception threshold intensity level for patient 12 (80), or determine the higher of the paresthesia threshold intensity level or the perception threshold intensity level for patient 12.

A paresthesia threshold intensity level may be a lowest determined electrical stimulation intensity level at which patient 12 first perceives paresthesia from the electrical stimulation delivered by IMD 14. A perception threshold intensity level may be a lowest determined electrical stimulation intensity level at which patient 12 first perceives the electrical stimulation delivered by IMD 14. In some cases, depending on the patient and/or the target electrical stimulation site within the patient, the patient may first perceive the electrical stimulation delivered by IMD 14 as paresthesia. Thus, in some cases, the perception threshold intensity level may be substantially the same (e.g., identical or nearly identical) as the paresthesia threshold intensity level. In other cases, however, a patient may first perceive the electrical stimulation as a sensation different than paresthesia. Thus, some cases, the perception threshold intensity level may be different than the paresthesia threshold intensity level. In these examples, a clinician may program IMD 14 and/or programmer 18 to use either the perception or paresthesia threshold intensity levels to select the electrical stimulation parameter with the technique shown in FIG. 8.

After determining one or both of the paresthesia threshold intensity level or the perception threshold intensity level, processing circuitry 30 may determine a strength-duration curve based on the determined one or both of the paresthesia or perception threshold intensity level and one or more selected electrical stimulation signal frequencies (82). A strength-duration curve may describe the relationship between a strength of electrical stimulation and duration, e.g., for a particular physiological response, such as a response below the paresthesia or perception threshold of patient 12. The strength of electrical stimulation may be a function of, for example, any one or more of the voltage or current amplitude value of the stimulation signal, frequency of stimulation signals, signal duration (e.g., pulse width in the case of stimulation pulses), duty cycle, frequency of recharge pulses (e.g., how many pulses are delivered before one or more recharge pulses are delivered), delay between stimulation pulses and recharge pulses, and the like.

For example of a strength duration curve is an amplitude-pulse width curve. The amplitude-pulse width curve may reflect, for a selected stimulation frequency, different combinations of amplitude and pulse width values that contribute to a stimulation field in a substantially similar manner. For example, the amplitude-pulse width curve may indicate that a first electrical stimulation signal with a first amplitude and a first pulse width, and a second electrical stimulation signal having a higher amplitude pulse with a shorter pulse width (i.e., shorter than the first pulse width) may both provide electrical stimulation therapy below the paresthesia or perception threshold of patient 12. Each position on the amplitude-pulse width curve, or each position within a particular range of positions along the amplitude-pulse width curve, may result in a substantially similar stimulation energy when the other therapy parameter values, such as a frequency, remain substantially constant (e.g., the other therapy parameter values may remain within a particular range of therapy parameter values, such as within a 10% window or less from the values defined by the therapy program). Thus, for a given stimulation frequency, the amplitude-pulse width curve may define, e.g., via the amplitude-pulse width combinations associated with the area under the curve and/or along the curve, the amplitude and pulse width combinations that provide electrical stimulation therapy having an intensity level below the paresthesia or perception threshold intensity level of patient 12.

For a given frequency in a range of about 1 Hz to about 1000 Hz), based on the strength-duration curve, processing circuitry 30 may determine the pulse width and amplitude combination that provides efficacious electrical stimulation therapy to patient 12 and also has a stimulation intensity below the paresthesia or perception threshold of patient 12 (84). Processing circuitry 30 may, automatically or in response to user input provided via programmer 18, control stimulation generating circuitry 34 to generate and deliver electrical stimulation therapy to patient 12 with the frequency associated with the strength-duration curve, a selected combination of electrodes 24, 26, and a plurality of pulse width and amplitude combinations along the strength-duration curve or below the amplitude-pulse width curve. Processing circuitry 30 may determine whether any of the selected pulse width and amplitude combinations provides efficacious electrical stimulation therapy for patient 12, e.g., based on patient 12 input or input from another entity received via programmer 18, based on input from sensing circuitry of IMD 14 or a separate sensing circuitry, or any combination thereof. Processing circuitry 30 may generate one or more therapy programs based on the one or more pulse width and amplitude combinations that provide efficacious electrical stimulation therapy to patient 12, together with the selected frequency and electrode combination (86).

In some examples in which stimulation generating circuitry 34 generates and delivers the high duty cycle electrical stimulation therapy via a plurality of sub-signals delivered via respective electrode combinations, processing circuitry 30 may determine a strength-duration curve for each electrode combination. Thus, for each electrode combination, the respective strength-duration curve may indicate a plurality of combinations of electrical stimulation parameters (e.g., amplitude and pulse width for a given frequency) that provide a charge per pulse below the paresthesia or perception threshold of patient 12. Based on the strength-duration curves, processing circuitry 30, alone or based on input from a clinician, may determine, for each of the electrode combinations, one or more therapy programs that provide a relatively high charge per pulse (e.g., the relatively highest charge per pulse that remains at or below the paresthesia or perception threshold of patient 12). Each therapy program may define a sub-signal. Processing circuitry 30, alone or based on input from a clinician, may then determine a frequency to interleave the two or more sub-signals.

In some examples, to determine the therapy programs, processing circuitry 30 may determine one or more test therapy programs that define relatively wide pulse widths and relatively low frequencies of the sub-signals, control stimulation generating circuitry 34 to generate and deliver electrical stimulation to patient 12 according to the test therapy programs, and, if the delivered electrical stimulation therapy is not sufficiently efficacious, processing circuitry 30 may modify one or more of the test therapy programs until the electrical stimulation provides efficacious stimulation therapy for patient 12. The efficacy of the electrical stimulation therapy can be based on input from patient 12, from one or more sensed physiological parameters, or any combination thereof. Processing circuitry 30 may modify one or more of the test therapy programs by, for example, incrementally narrowing the pulse width (e.g., by a predetermined increment) and/or incrementally increasing the frequency (e.g., by a predetermined increment).

Processing circuitry 30 may store the one or more therapy programs 40 in memory 32 of IMD 12 or a memory of another device for later delivery of electrical stimulation therapy to patient 12 (86). Processing circuitry 30 may control stimulation generating circuitry 34 to generate and deliver electrical stimulation therapy to patient 12 in accordance with the one or more therapy programs 40.

In some cases, therapeutic efficacy of electrical stimulation therapy delivered by IMD 14 may change as the patient posture state (e.g., a particular patient posture or a combination of posture and activity) changes. Efficacy may refer to a combination of complete or partial alleviation of symptoms alone, or in combination with no side effects or an acceptable or tolerable degree of undesirable side effects. In some examples, processing circuitry 30 of IMD 14 may be configured to adjust one or more therapy parameter values based on different postures and/or activities engaged by patient 12 to maintain effective therapy, e.g., by selecting select different therapy programs based on a posture state of patient 12. In these examples, processing circuitry 30 may determine the paresthesia or perception threshold of patient 12 for each of a plurality of different posture states and determine one or more therapy programs 40 for each of the posture states using the technique shown in FIG. 8 based on the respective paresthesia or perception threshold.

Figure 9:
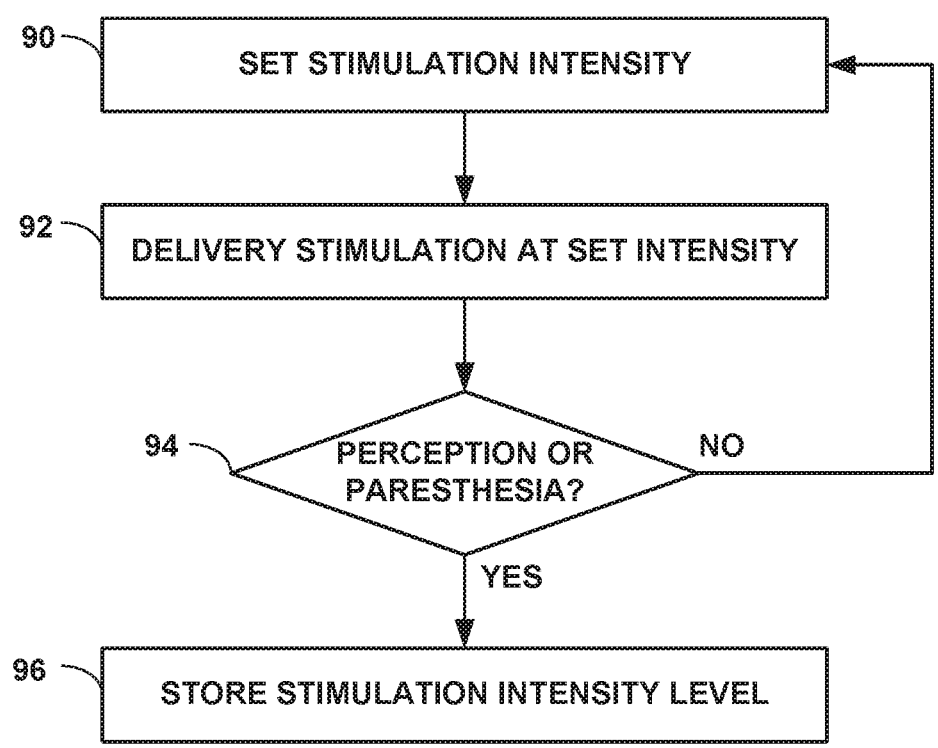
FIG. 9 is a flow diagram of an example method of determining a perception or paresthesia threshold intensity level for a patient.

FIG. 9 is a flow diagram of an example technique by which processing circuitry 30 of IMD 14 can determine at least one of the perception or paresthesia threshold intensity level for patient 12. In some examples, processing circuitry 30 is configured to determine the perception threshold intensity level, while in other examples, processing circuitry 30 is configured to determine the paresthesia threshold intensity level or both the perception and paresthesia threshold intensity level.

The perception or paresthesia threshold intensity level can be patient-specific, as well as specific to a target tissue site within patient 12. Thus, a perception or paresthesia threshold intensity level can be determined for each target tissue site to whith IMD 14 delivers stimulation therapy. In some examples, processing circuitry 30 of programmer 18 may implement the technique illustrated in FIG. 9 automatically, e.g., without user intervention or control after initiating the technique. In other examples, processing circuitry 30 may implement the technique illustrated in FIG. 9 under control of a user, such as a clinician, who controls processing circuitry 30 via programmer 18. While FIG. 9 is described with respect to processing circuitry 30 of IMD 14, in other examples, processing circuitry 50 of programmer 18 may perform any part of the technique described with respect to FIG. 9, alone or in combination with processing circuitry 30 of IMD 14.

In accordance with the technique shown in FIG. 9, processing circuitry 30 sets stimulation parameter values such that the stimulation parameter values define a relatively low stimulation intensity, e.g., an intensity below an expected perception or paresthesia threshold intensity (90). The initial stimulation parameter values may be selected by a clinician in some examples. In some examples in which processing circuitry 30 controls stimulation generating circuitry 34 to generate and deliver stimulation to patient 12 in the form of electrical pulses, the stimulation parameters include at least one of a voltage or current amplitude, a pulse width, a pulse rate, or a duty cycle. In examples in which processing circuitry 30 controls stimulation generating circuitry 34 to deliver stimulation to patient 12 in the form of a continuous waveform, the stimulation parameters include at least one of a voltage amplitude, a current amplitude, a frequency, a waveform shape, or a duty cycle.

In either case, processing circuitry 30 sets the stimulation parameters to respective values to define a stimulation intensity, and controls stimulation generating circuitry 34 to deliver stimulation to patient 12 at the set stimulation intensity (defined by the selected stimulation parameter values) (92). During therapy delivery or after stimulation generating circuitry 34 delivers stimulation to patient 12, processing circuitry 30 determines whether patient 12, a clinician, or patient caretaker has provided input indicating patient 12 has perceived the electrical stimulation or indicating paresthesia resulted from the electrical stimulation (94). Patient 12, the clinician, or patient caretaker can provide the input, e.g., via user interface 54 of programmer 18 or directly via IMD 14. For example, a motion sensor can be integrated into or on a housing of IMD 14, and the motion sensor can be configured to generate a signal that is indicative of patient 12 tapping IMD 14 through the skin. The number, rate, or pattern of taps may be associated with the input indicative of stimulation perception or paresthesia, and processing circuitry 30 may identify the tapping by patient 12 to determine when patient input is received. When the input is received via user interface 54 of programmer 18, processing circuitry 50 of programmer 18 may transmit a signal indicative of the input to IMD 14 via the respective telemetry circuitry 56, 36.

When processing circuitry 30 has not received an indication of the input indicative of the stimulation perception or paresthesia within a predetermined time period during or immediately after delivery of the stimulation according to the selected stimulation intensity ("NO" branch of block 94), processing circuitry 30 again sets the stimulation intensity, e.g., by adjusting at least one stimulation parameter value to increase a stimulation intensity of the stimulation signal (90). For example, processing circuitry 30 may increase a voltage amplitude or a current amplitude to increase the stimulation intensity. In some examples, processing circuitry 30 changes a value of only one of the stimulation parameters while the remaining parameters are kept approximately constant. The stimulation parameter that is selected may be known to affect stimulation intensity. In other examples, processing circuitry 30 may adjust a combination of two or more stimulation parameters to increase stimulation intensity.

After modifying the one or more stimulation parameter values, processing circuitry 30 controls stimulation generating circuitry 34 to deliver stimulation to patient 12 using the newly defined stimulation parameter values (92). In this way, processing circuitry 30 can implement an iterative procedure to determine the perception or paresthesia threshold intensity for patient 12, and, in some examples, for a specific target tissue site within patient 12.

In response to not receiving input indicative of patient perception or paresthesia is received within a predetermined time period during or immediately after delivery of the stimulation according to the selected stimulation intensity ("NO" branch of block 94), processing circuitry 30 may again adjust at least one stimulation parameter value to increase a stimulation intensity of the stimulation signal (90). This process may repeat until processing circuitry 30 receives input indicative of patient perception or paresthesia within a predetermined time period during or immediately after delivery of the stimulation according to the selected stimulation intensity. In response to receiving the input ("YES" branch of block 94), processing circuitry 30 may store the stimulation intensity level as the patient perception threshold intensity level and/or paresthesia threshold intensity level (depending on the whether the response indicates patient perception of the electrical stimulation or resulting paresthesia, respectively) in memory 32 of IMD 14 (FIG. 2) or in another memory (e.g., memory 52 of programmer 18) (96).

In addition, processing circuitry 30 may define stimulation parameter values for the therapy programs 40 (FIG. 2) for providing the high duty cycle electrical stimulation techniques described herein based on the determined patient perception threshold intensity level and/or paresthesia threshold intensity level, e.g., using the technique described with respect to FIG. 8. For example, processing circuitry 30 may define stimulation parameter values for the therapy programs 40 (FIG. 2) that result in a stimulation intensity level less than or equal to one or both of the patient perception threshold intensity level or paresthesia threshold intensity level.

While the techniques described above are primarily described as being performed by processing circuitry 30 of IMD 14 or processing circuitry 50 of programmer 18, in other examples, one or more other processing circuitry components may perform any part of the techniques described herein alone or in addition to processing circuitry 30 or processing circuitry 50, Thus, reference to "processing circuitry" may refer to "one or more processors." Likewise, "one or more processors" or processing circuitry may refer to a single processor or multiple processors in different examples.

Figure 10A:
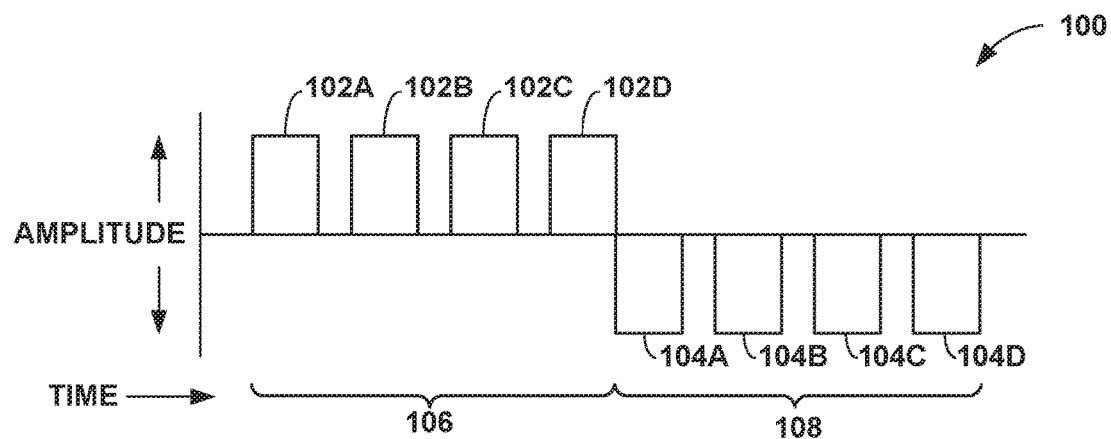
FIGS. 10A-10C are graphs illustrating example high duty electrical stimulation waveforms where one or more recharge signals are delivered subsequent to the plurality of electrical stimulation pulses being delivered.
Figure 10B:
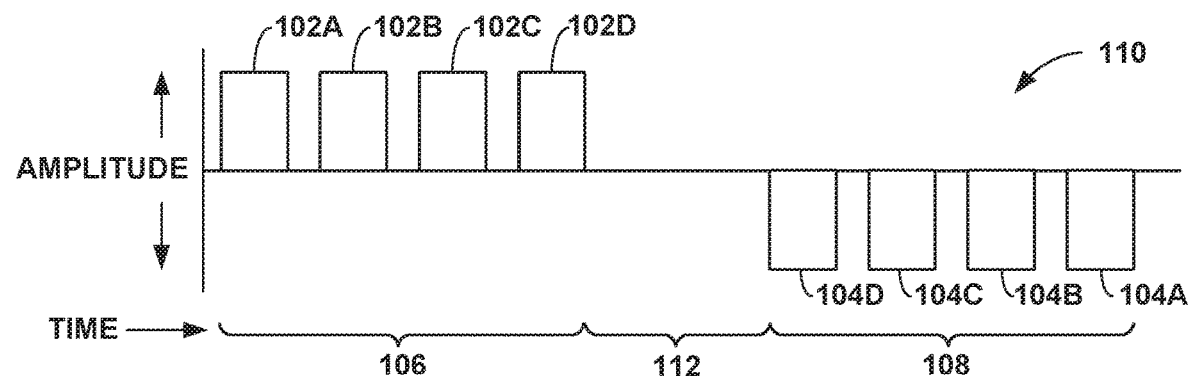
Figure 10C:
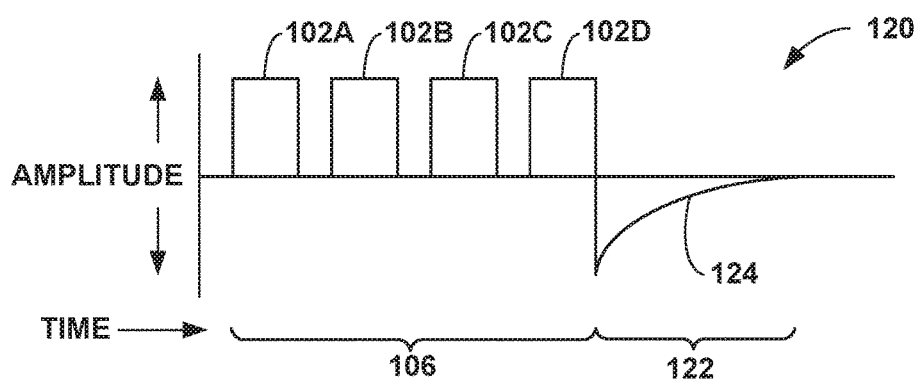

FIGS. 10A-10C are graphs that illustrate examples of high duty electrical stimulation signals where one or more recharge pulses are delivered subsequent to each of a plurality of electrical stimulation pulses that have been delivered. FIG. 10A depicts a first signal 100 with four electrical stimulation pulses 102A-D (collectively "electrical stimulation pulses 102") that are followed by four recharge pulses 104A-D (collectively "recharge pulses 104"). Electrical stimulation pulses 102 are generated and delivered in an order of 102A, 102B, 102C, and 102D over period of time 106. Electrical stimulation pulses 102 may have a duty range of about 5% to about 50%, for example.

In some examples, each electrical stimulation pulses 102 of the signal 100 may have substantially similar pulse widths as the other electrical stimulation pulses 102 of the signal 100. In other examples, each electrical stimulation pulse 102 may have a different pulse width in comparison to the other electrical stimulation pulses 102 of the signal 100, or some electrical stimulation pulses 102 of the signal 100 may share pulse widths while other electrical stimulation pulses 102 of the signal 100 have unique pulse widths.

In some examples, stimulation generation circuitry 34 may individually and sequentially generate and then deliver each electrical stimulation pulse 102. Put differently, in some examples stimulation generation circuitry 34 may neither generate nor deliver a second electrical pulse until a first electrical pulse is both generated and delivered. In such examples, electrical pulse 102A may be generated and then delivered, after which electrical pulse 102B may be generated and then delivered, after which electrical pulse 102C may be generated and then delivered, after which electrical pulse 102D may be generated and then delivered. In other examples, IMD 14 may be able to generate a plurality of electrical stimulation pulses 102 simultaneously (e.g., as a result of multiple current sources). In such examples, a plurality or all electrical stimulation pulses 102 may be generated simultaneously, after which respective electrical stimulation pulses 102 may be delivered according to respective stimulation programs.

Each electrical stimulation pulse 102 of the signal 100 may be delivered according to a single stimulation program. Alternatively, the electrical stimulation pulses 102 of the signal 100 may be delivered according to a plurality of stimulation programs. In some situations, each electrical stimulation pulse 102 of the signal 100 may be delivered according to a different stimulation program. In this manner, stimulation pulses 102 may be delivered from common electrodes or from different electrodes.

As depicted in FIG. 10A, the plurality of electrical stimulation pulses 102 may be followed by a respective plurality of recharge pulses 104. Each recharge pulse 104 may correspond to one of the preceding electrical stimulation pulses 102, such that each electrical stimulation pulse 102 is paired with a respective recharge pulse 104 that may be specifically selected for its associated stimulation pulse 102. Recharge pulses 104 may be delivered over period of time 108. An electrical stimulation pulse 102 and recharge pulse 104 that are paired may both be delivered by the same electrode and have opposite amplitudes or polarities. As depicted in FIG. 10A, the recharge pulses 104 may be active pulses (e.g., in comparison to passive charges). An active pulse may be a pulse that is delivered with predefined parameters such as predefined amplitude and pulse width to provide the charge balance to the tissue of the patient 12. Recharge pulses 104 may have different pulse amplitudes and/or pulse widths that may or may not correspond to the amplitudes and pulse widths of the respective stimulation pulses 102. A passive pulse or passive signal may alternatively be used alone or in conjunction with active pulses and is described with respect to FIG. 10C.

In some examples, recharge pulse 104A may be paired with electrical stimulation pulse 102A, while recharge pulse 104B is paired with electrical stimulation pulse 102B, recharge pulse 104C is paired with electrical stimulation pulse 102C, and recharge pulse 104D is paired with electrical stimulation pulse 102D. In some examples, recharge pulses 104 may be delivered in the same order as their respective electrical stimulation pulses 102, as in signal 100. Alternatively, the recharge pulses 104 may be delivered in a different order than their respective electrical stimulation pulse, such that the time period between the stimulation pulses 102 and their respective recharge pulse 104 is different. As depicted in FIG. 10A, recharge pulses 104 may be delivered immediately upon the delivery of the final electrical stimulation pulse 102D. In some examples, period of time 106 may be substantially similar to period of time 108.

In some examples, each electrical stimulation pulse 102 of the signals 100 is delivered to a different electrode. In other examples, two or more electrical stimulation pulse 102 of the signals 100 may be delivered to the same electrode. For example, electrical stimulation pulses 102A and 102C may be delivered to a first electrode, while electrical stimulation pulse 102B and 102D are delivered to a second electrode. Alternatively, electrical stimulation pulse 102A may be delivered to a first electrode, while electrical stimulation pulses 102B-D are delivered to a second electrode. Other combinations of electrical stimulation pulses 102 being delivered to different combinations of electrodes are also contemplated.

FIG. 10B depicts another example signal 110 comprising a plurality of high duty electrical stimulation pulses 102 being generated and delivered followed by a plurality of recharge pulses 104. The electrical stimulation pulses 102 and recharge pulses 104 of FIG. 10B may be substantially similar to the electrical stimulation pulses 102 and recharge pulses 104 of FIG. 10A, such that the same electrical stimulation pulses 102 are paired with the same respective recharge pulses 104. Signal 110 includes withholding the recharge pulse(s) 104 for period of time 112 (e.g., recharge pulse(s) may be withheld for one millisecond after electrical stimulation pulses 102 are delivered). One or more recharge pulses 104 may be withheld for a period of time 112 of any length. In some examples, the withholding period of time 112 may be shorter than the period of time 106 it takes to generate and deliver the electrical stimulation pulses 102. In other examples, the withholding period of time 112 may be longer or equal to the period of time 106 it takes to generate and deliver the electrical stimulation pulses 102. Period of time 112 may be selected according to how long the electrical charge is intended to be maintained in the tissue prior to delivering the respective recharge pulses 104.

The withholding period of time 112 may be a function of other elements of the signal 110. For example, the withholding period of time 112 may be related to (e.g., longer or shorter as a result of) the number of pulses 102 within the preceding plurality of pulses 102, the length of the period of time 106 over which the plurality of pulses was delivered, the amplitude of the plurality of pulses 102 of the pulses 102, or other factors. The withholding period of time 112 may be defined by one or more stimulation programs of the signal 110.

In some examples, as depicted in signal 110, recharge pulses 104 are delivered in a different order than their respective electrical stimulation pulses 102. For example, in signal 110, electrical stimulation pulse 102A is delivered first (e.g., relative to the other electrical stimulation pulses 102), while paired recharge pulse 104A is delivered last (e.g., relative to the other recharge pulses 104). The alternate order of recharge pulses 104 (e.g., alternate in comparison to paired electrical stimulation pulses) depicted in signals 110 is for illustrative purposes only; other alternate orders are contemplated.

FIG. 10C depicts another example signal 120 comprising a plurality of high duty electrical stimulation pulses 102 being generated and delivered followed by one recharge pulse 124. In some examples, the recharge pulse 124 is a passive recharge pulse. The passive recharge pulse 124 may allow for the built-up charge of the electrical stimulation pulse 102 to bleed back to the baseline amplitude through the respective electrode(s) of the passive recharge pulse(s) selected by IMD 14. Recharge pulse 124 is shown in FIG. 10C as an exponentially decaying slope to indicate that the amplitude of recharge pulse 124 may decline over time as the amount of charge is reduced in the tissue. The passive recharge of recharge pulse 124 may have an undefined amplitude and/or pulse width. In other words, IMD 14 may connect the desired electrodes to ground and allow the charge imbalance to sink back to IMD 14. In some examples, recharge pulse 124 may not always return the charge to neutral when a new series of stimulation pulses is delivered prior to the charge being balanced. It is noted that the amplitude of recharge pulse 124 may have a greater initial amplitude, and/or last for a longer period of time, when multiple stimulation pulses 102 are delivered within intervening recharge pulses. In other examples (not depicted), the single recharge pulse 124 may be an active pulse.

In some examples, as depicted in signal 120, a single passive recharge pulse 124 may act to counter the charge for a plurality of electrical stimulation pulses 102 that preceded the passive recharge pulse 124. In certain examples, one passive recharge pulse 124 may counter the charge for all of the preceding plurality of electrical stimulation pulses 102. In other examples (not depicted), each electrical stimulation pulse 102 may be paired with a respective passive recharge pulse 124 that is delivered following the delivery of the plurality of electrical stimulation pulses 102. In examples where stimulation pulses 102 are delivered from different electrodes, recharge pulse 124 may represent recharge pulses provided for each of those electrodes in which pulses 102 were previously delivered.

The passive recharge pulse 124 may last for a period of time 122. As depicted in signals 120, the passive recharge pulse 124 may be delivered immediately after period of time 106 over which the electrical stimulation pulses 102 are delivered. In other examples (not depicted), the passive recharge pulse 124 may be withheld similar to the signal 110 of FIG. 10B for a period of time 112.

Figure 11:
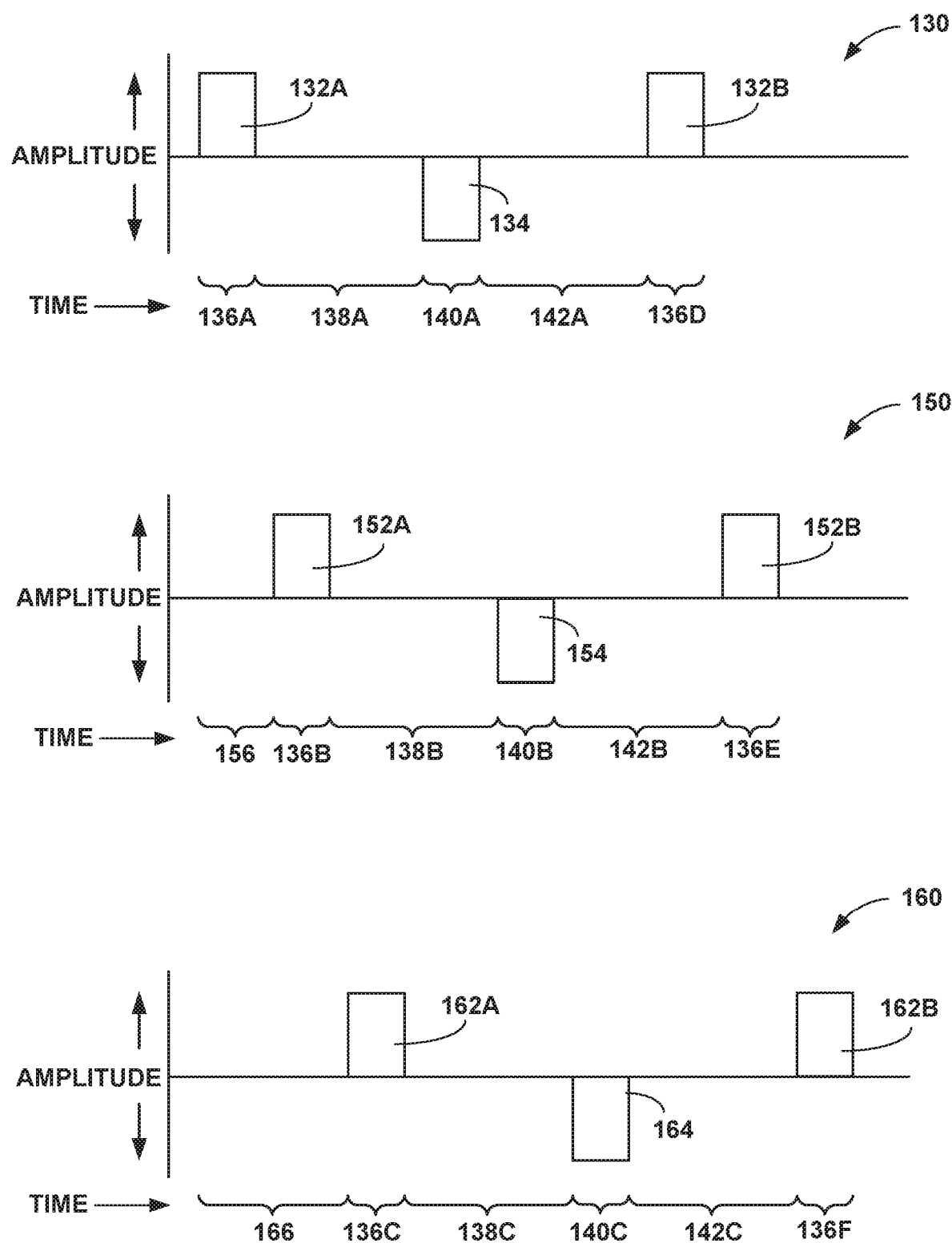
FIG. 11 illustrates example waveforms of a plurality of programs that are acting together to deliver a plurality of electrical stimulation pulses to a patient.

FIG. 11 illustrates an example of signals 130, 150, 160 of respective therapy programs that are acting together to deliver a plurality of electrical stimulation pulses to a patient. Each program may specify certain parameter values for the pulses and electrode combinations such that signals 103, 150, and 160 are delivered via different electrode combinations. Signal 130 comprises two electrical stimulation pulses 132A, 132B (collectively "electrical stimulation pulses 132") and a recharge pulse 134, while signal 150 comprises two electrical stimulation pulses 152A, 152B (collectively "electrical stimulation pulses 152") and a recharge pulse 154, and signal 160 comprises two electrical stimulation pulses 162A, 162B (collectively "electrical stimulation pulses 162") and a recharge pulse 164. IMD 14 may deliver signal 130 by delivering electrical stimulation pulses 132 according to a first stimulation program, while IMD 14 may deliver signal 150 by delivering electrical stimulation pulses 152 according to a second stimulation program, and IMD 14 may deliver signal 160 by delivering electrical stimulation pulses 162 according to a third stimulation program.

Electrical stimulation pulses 132, 152, 162 may be high-duty pulses (or a part of high-duty cycle stimulation therapy) as described herein. In some examples, electrical stimulation pulses 132, 152, 162 of the three signals 130, 150, 160 may be substantially similar (e.g., having substantially similar pulse widths, amplitudes, etc.). In other examples, some of the electrical stimulation pulses 132, 152, 162 may be substantially similar, while other electrical stimulation pulses 132, 152, 162 may be relatively unique. In certain examples, each signal 130, 150, 160 may have relatively unique electrical stimulation pulses 132, 152, 162, such that few or no signals 130, 150, 160 may include electrical stimulation pulses 132, 152, 162 that are substantially similar to electrical stimulation pulses 132, 152, 162 of another signal 130, 150, 160.

The programs defining each of the three signals 130, 150, 160 may coordinate the delivery of the electrical stimulation pulses 132, 152, 162 by specific timing of each electrical stimulation pulse 132, 152, 162. For example, a first electrical stimulation pulse 132A may be delivered over a period of time 136A according to a first stimulation program. A second electrical stimulation pulse 152A may be delivered over a period of time 136B after a delay of a period of time 156 according to a second stimulation program. In some examples, as depicted in FIG. 11, period of time 156 preceding the delivery of the second electrical stimulation pulse 152A may be slightly longer than the period of time 136A during which IMD 14 delivers the first electrical stimulation pulse 132A, such that there is a slight pause between the first electrical stimulation pulse 132A and the second electrical stimulation pulse 152A. In other examples (not depicted), the period of time 156 before the second pulse 152A is substantially similar to the period of time 136A during which IMD 14 delivers the first electrical stimulation pulse 132A, such that the second electrical stimulation pulse 152A is delivered virtually immediately after the first electrical stimulation pulse 132A is delivered.

Similarly, IMD 14 may deliver a third electrical stimulation pulse 162A over a period of time 136C after a delay of a period of time 166 according to a third stimulation program. The period of time 166 before the third electrical stimulation pulse 162 is delivered may be slightly longer than the sum of the respective durations 136A, 136B of the first electrical stimulation pulse 132A and the second electrical stimulation pulse 152A. In other words, the period of time 166 preceding the delivery of the third electrical stimulation pulse 162A may result in the third pulse 162A being delivered following a slight pause after the second electrical stimulation pulse 152A.

Subsequent to the third electrical stimulation pulse 162A being delivered, IMD 14 may deliver a first recharge pulse 134 for the first electrical stimulation pulse 132A according to the first stimulation program. Stimulation generation circuitry 34 may deliver the first recharge pulse 134 according to the first stimulation program, such that first recharge pulse is delivered a period of time 138A after the first electrical stimulation pulse 132A is delivered. The period of time may allow for IMD 14 to deliver both the second and third pulses 152A 162A before delivery of the first recharge pulse 134. Similarly, as depicted in FIG. 11, subsequent to the first recharge pulse 134 being delivered, IMD 14 may deliver a second recharge pulse 154 for the second pulse 152A according to the second stimulation program and deliver a third recharge pulse 164 for the third pulse 162A according to the third stimulation program.

As depicted in the example of FIG. 11, IMD 14 delivers recharge pulses 134, 154, 164 with a slight pause between each recharge pulse. In other examples, each recharge pulse may be delivered virtually immediately after a respective preceding recharge pulse or electrical stimulation pulse. In yet other examples, IMD 14 may deliver each recharge pulse 134, 154, 164 at substantially the same time. In some examples (not depicted), IMD 14 may deliver recharge pulses 134, 154, 164 according to a plurality of stimulation programs in a different order than the order in which the first pulses 132A, 152A, 162A are delivered, similar to FIG. 10B. Though FIG. 11 depicts each period of time 138A, 138B, 138C between respective electrical stimulation pulses 132A, 152A, 162A and recharge pulses 134, 154, 164 as being substantially similar, in other examples the periods of time 138A, 138B, 138C between pulse and recharge may have different durations between each or some stimulation programs.

Though FIG. 11 depicts recharge pulses 134, 154, 164 as three ordered active recharge pulses, it is to be understood that other orders of different kinds of recharge pulses are contemplated. For example, recharge pulses 134, 154, 164 may be passive recharges that are delivered at much the same time as the recharge pulses 134, 154, 164. Alternatively, recharge pulses 134, 154, 164 may be either active pulses or passive pulses that all are delivered simultaneously, such as over the period of time 140A.

Subsequent to the recharge pulses 134, 154, 164 being delivered, IMD 14 may continue to deliver another round of electrical stimulation pulses 132B, 152B 162B according to the first, second, and third stimulation programs. As depicted in FIG. 11, IMD 14 may deliver electrical stimulation pulse 132B a period of time 142A after the first recharge pulse 134, while electrical stimulation pulse 152B is delivered a period of time 142B after the second recharge pulse 154, and electrical stimulation pulse 162B is delivered a period of time 142C after the third recharge pulse 164. Put differently, the fourth 132B, fifth 152B, and sixth 162B electrical stimulation pulses may be delivered according to respective programs in the same order as the first 132A, second 152A and third 162A electrical stimulation pulses. In other examples (not depicted), a second round of electrical stimulation pulses may include the second pulses 132B. 152B. 162B being delivered in a different order than the order in which the first pulses 132A, 152A, 162A were delivered (e.g., electrical stimulation pulses 132, 152, 162 may be delivered in the order of 152B, then 132B, then 162B). In this way, a plurality of stimulation programs may independently provide a plurality of electrical stimulation pulses that are delivered before one or more recharge pulses for the plurality of electrical stimulation pulses.

Figure 12:
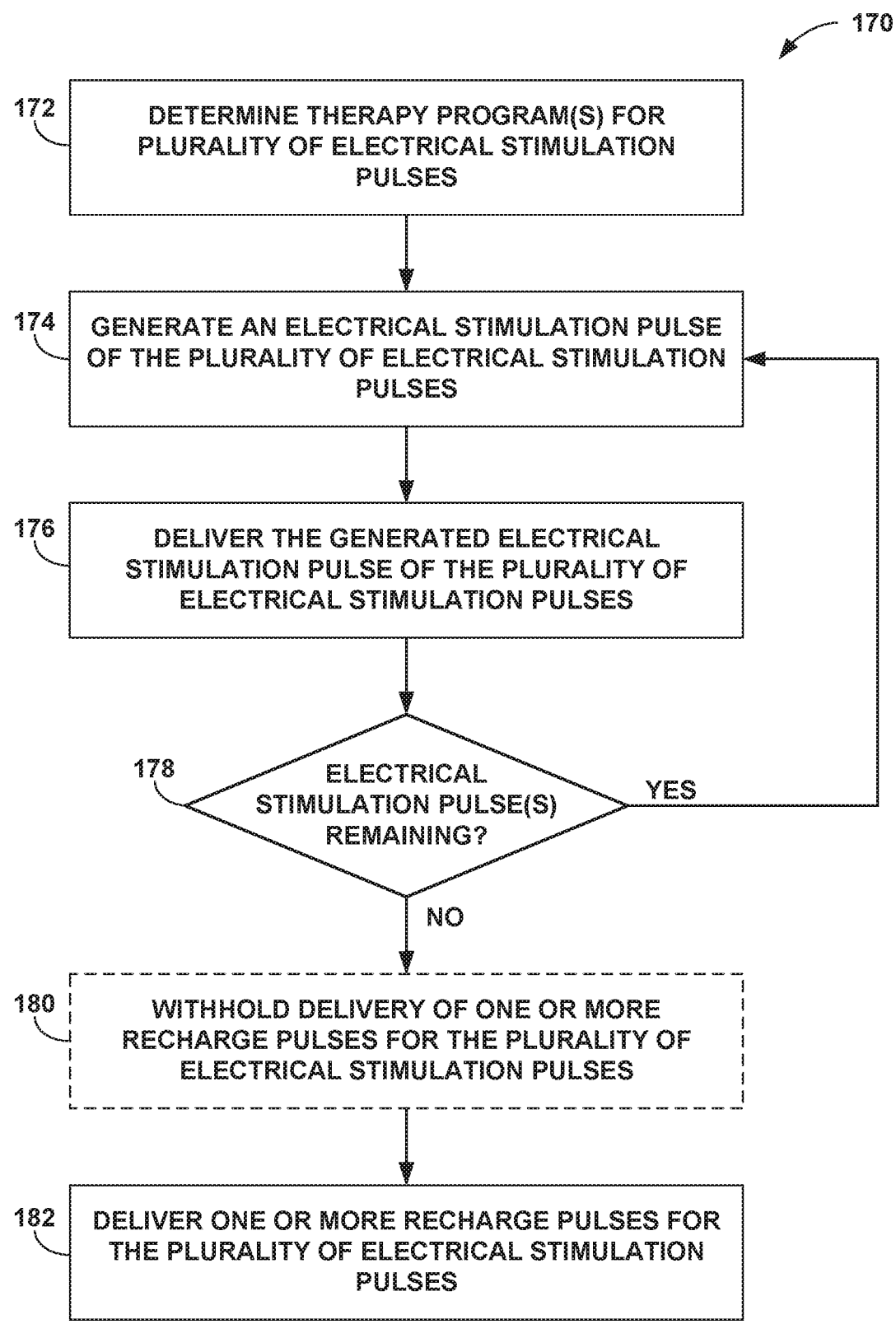
FIG. 12 is a flow diagram of an example method of delivering one or more recharge signals for a plurality of electrical stimulation pulses subsequent to each of the plurality of electrical stimulation pulses being delivered.

FIG. 12 is a flow diagram of an example method 170 for delivering one or more recharge signals for a plurality of electrical stimulation pulses subsequent to each of the plurality of electrical stimulation pulses being delivered. The electrical stimulation pulses of the method 170 may be similar to the high duty pulses described above, while the recharge pulses may be similar to the recharge pulses described above. Method 170 will be described with respect to processing circuitry 30 and stimulation generating circuitry 34 of IMD 14. However, in other examples, at least some or all of method 170 may be performed by other components of IMD 14 or by components of other devices, such as processing circuitry 50 of external programmer 50.

In the example of FIG. 12, processing circuitry 30 determines one or more therapy programs for the plurality of electrical stimulation pulses (172). The one or more therapy programs may include a plurality of electrical stimulation pulses with a duty cycle in a range of about 5% to about 50%. Processing circuitry 30 may select the appropriate therapy programs 40 stored in memory 32. In other examples, processing circuitry 30 may determine the therapy programs by generating therapy programs similar to step 86 discussed with respect to FIG. 8. Stimulation generating circuitry 34 generates a first electrical stimulation pulse (174). The stimulation generating circuitry 34 may generate the first electrical stimulation pulse as described herein. The stimulation generating circuitry 34 may generate the first electrical stimulation pulse according to a first program. The stimulation generating circuitry delivers the first electrical stimulation pulse (176). The stimulation generating circuitry may deliver the first electrical stimulation pulse to a first electrode that is coupled to a lead of the medical device. The first electrical stimulation pulse may have a first pulse width.

At this point processing circuitry 30 may determine whether or not there are more electrical stimulation pulses to generate and deliver before delivering one or more recharge pulses (178). In some examples, processing circuitry 30 may be determine that there are more electrical stimulation pulses to generate and deliver ("YES" branch of block 178), In such examples, stimulation generating circuitry 34 generates (174) and delivers (176) a second electrical stimulation pulse. The stimulation generating circuitry 34 may generate and deliver the second electrical stimulation pulse according to the first program or according to a different program. The stimulation generating circuitry 34 may generate and deliver the second stimulation pulse after the first stimulation pulse is delivered. The second stimulation pulse may have a pulse width that is different than or substantially similar to the first pulse width. The stimulation generating circuitry 34 may deliver the second stimulation pulse to a second electrode rather than the first electrode of the lead of the medical device.

In some examples, the power source 38 of IMD 14 may include a plurality of current sources that are able to provide numerous current sources for the electrical stimulation pulses. In such examples, it may be possible to generate and/or deliver numerous electrical stimulation pulses of the plurality of electrical stimulation pulses simultaneously or near simultaneously. For example, the stimulation generating circuitry 34 may generate (174) and deliver (176) the first and second electrical stimulation pulses simultaneously (e.g., wherein the first electrical stimulation pulse is driven by a first current source and the second electrical stimulation pulse is driven by a second current source), after which processing circuitry 30 may determine (178) that there are more electrical stimulation pulses of the plurality of electrical stimulation pulses ("YES" branch of block 178), in response to which stimulation generating circuitry 34 may simultaneously generate (174) and deliver (176) a third and fourth electrical stimulation pulse, for example.

Eventually, after stimulation generating circuitry 34 generates and delivers a plurality of electrical stimulation pulses are generated and delivered, processing circuitry 30 determines that all electrical stimulation pulses of the plurality of electrical stimulation pulses have been generated and delivered ("NO" branch of block 178). It is to be understood that the plurality of electrical stimulation pulses may comprise any number of electrical stimulation pulses that is greater or equal to two, such as three, four, five, ten, or more pulses.

In some examples, processing circuitry 30 may determine that the two electrical stimulation pulses discussed above may be the only two electrical stimulation pulses of the plurality of electrical stimulation pulses ("NO" branch of block 178). In response to this determination, stimulation generating circuitry 34 may deliver one or more recharge pulses. The one or more recharge pulses may be for the first and second electrical stimulation pulses, such that the one or more recharge pulses cancel out the charge placed upon the tissue as a result of the first and second electrical stimulation pulses. The stimulation generating circuitry 34 may withhold one or more recharge pulses for a period of time (180) before delivering the one or more recharge pulses (180). Withholding the one or more recharge pulses may allow for the charge of the first and second electrical stimulation pulses to further build upon the tissue of the patient as desired.

The one or more recharge pulses may be active or passive. Active recharge pulses may be pulses that have defined amplitudes and/or pulse widths, which may or may not be the same amplitude and pulse width of a respective pulse of the plurality of pulses but of the opposite polarity/amplitude of the respective pulse. Passive recharge pulses may be the equivalent of a "ground" to the respective electrode that allows the charge of the respective electrical stimulation pulse to bleed out through the respective electrode. In this manner, passive signals or pulses may not have defined amplitudes and/or durations.

The one or more recharge pulses may include a plurality of recharge pulses, where each recharge pulse is paired with one or more electrical stimulation pulses. Where there is a plurality of recharge pulses, stimulation generating circuitry 34 may deliver the recharge pulses in the same order or in a relatively different order than the order in which the original electrical stimulation pulses were delivered. The order of the recharge pulses, whether the same or different than respective electrical stimulation pulses, may be defined by one or more programs. Alternatively, where there is a plurality of recharge pulses, each of the recharge pulses may be delivered simultaneously.

The techniques described in this disclosure, including those attributed to IMD 14, programmer 18, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit, Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor" or "processing circuitry" as used herein may refer to one or more of any of the foregoing structure or any other structure suitable for implementation of the techniques described herein.

In addition, in some aspects, the functionality described herein may be provided within dedicated hardware and/or software modules. Depiction of different features as circuitry or units is intended to highlight different functional aspects and does not necessarily imply that such circuitry or units must be realized by separate hardware or software components. Rather, functionality associated with one or more circuitry or units may be performed by separate hardware or software components, or integrated within common or separate hardware or software components.

Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The following paragraphs described examples consistent with the present disclosure. In one example a method comprises generating, by a medical device, a plurality of electrical stimulation pulses having a duty cycle in a range of about 5% to about 50%, wherein the plurality of electrical stimulation pulses have a stimulation intensity less than at least one of a perception threshold or a paresthesia threshold of a patient, delivering, by the medical device, a first electrical stimulation pulse of the plurality of electrical stimulation pulses to the patient, subsequent to delivering the first electrical stimulation pulse, delivering, by the medical device, a second electrical stimulation pulse of the plurality of electrical stimulation pulses to the patient, and subsequent to delivering the first pulse and the second pulse, delivering, by the medical device, one or more recharge pulses for at least the first electrical stimulation pulse and the second electrical stimulation pulse.

EXAMPLE 2

The method of example 1, wherein the first electrical stimulation pulse comprises a first pulse width different from a second pulse width of the second electrical stimulation pulse.

EXAMPLE 3

The method of any of examples 1 to 2, wherein delivering the first electrical stimulation pulse comprises delivering the first electrical stimulation pulse from a first electrode of one or more leads coupled to the medical device, and wherein delivering the second electrical stimulation pulse comprises delivering the second electrical stimulation pulse from a second electrode of the one or more leads coupled to the medical device, wherein the first electrode is different than the second electrode.

EXAMPLE 4

The method of any of examples 1 to 2, wherein delivering the first electrical stimulation pulse comprises delivering the first electrical stimulation pulse from an electrode of a lead coupled to the medical device, and wherein delivering the second electrical stimulation pulse comprises delivering the second electrical stimulation pulse from the electrode of the lead.

EXAMPLE 5

The method of example 4, the method further comprising, subsequent to delivering the second electrical stimulation pulse and prior to delivering the one or more recharge pulses, delivering, by the medical device, a third electrical stimulation pulse of the plurality of electrical stimulation pulses to the patient from a second electrode coupled to the medical device.

EXAMPLE 6

The method of any of examples 1 to 5, the method further comprising withholding the delivery of the one or more recharge pulses for an amount of time following the delivery of the second electrical stimulation pulse.

EXAMPLE 7

The method of any of examples 1 to 6, wherein delivering the one or more recharge pulses further comprises simultaneously delivering, by the medical device, both a first recharge pulse of the one or more recharge pulses for the first electrical stimulation pulse and a second recharge pulse of the one or more recharge pulses for the second electrical stimulation pulse.

EXAMPLE 8

The method of any of examples 1 to 6, wherein delivering the one or more recharge pulses further comprises: delivering, by the medical device, a first recharge pulse of the one or more recharge pulses for the first electrical stimulation pulse; and subsequent to delivering the first recharge pulse, delivering, by the medical device, a second recharge pulse of the one or more recharge pulses for the second electrical stimulation pulse.

EXAMPLE 9

The method of any of examples 1 to 6, wherein delivering the one or more recharge pulses further comprises: delivering, by the medical device, a first recharge pulse of the one or more recharge pulses for the second electrical stimulation pulse; and subsequent to delivering the first recharge pulse, delivering, by the medical device, a second recharge pulse of the one or more recharge pulses for the first electrical stimulation pulse.

EXAMPLE 10

The method of any of examples 1 to 6, wherein delivering the one or more recharge pulses further comprises delivering, by the medical device, a recharge pulse of the one or more recharge pulses for both the first electrical stimulation pulse and the second electrical stimulation pulse.

EXAMPLE 11

The method of any of examples 1 to 10, wherein the medical device generates the plurality of electrical stimulation pulses according to a first stimulation program and second stimulation program, wherein the stimulation program defines the first electrical stimulation pulse, and wherein the second stimulation program defines the second electrical stimulation pulse.

EXAMPLE 12

The method of any of examples 1 to 11, wherein delivering the one or more recharge pulses comprises delivering ore or more passive recharge pulses.

EXAMPLE 13

The method of any of examples 1 to 11, wherein delivering the one or more recharge pulses comprises delivering one or more active recharge pulses having predetermined pulse amplitudes and pulse widths.

EXAMPLE 14

The method of any of examples 1 to 12, wherein the first electrical stimulation pulse and the second electrical stimulation pulse comprise a first polarity, and wherein the one or more recharge pulses comprise a second polarity opposite the first polarity.

EXAMPLE 15

A system comprising a plurality of electrodes; stimulation generation circuitry configured to generate and deliver electrical stimulation therapy to a patient; and processing circuitry configured to control the stimulation generation circuitry to: generate a plurality of electrical stimulation pulses having a duty cycle in a range of about 5% to about 50%, wherein the plurality of electrical stimulation pulses have a stimulation intensity less than at least one of a perception threshold or a paresthesia threshold of a patient; deliver a first electrical stimulation pulse of the plurality of electrical stimulation pulses to the patient; subsequent to delivering the first electrical stimulation pulse, deliver a second electrical stimulation pulse of the plurality of electrical stimulation pulses to the patient; and subsequent to delivering the first pulse and the second pulse, deliver one or more recharge pulses for at least the first electrical stimulation pulse and the second electrical stimulation pulse.

EXAMPLE 16

The system of example 15, wherein the first electrical stimulation pulse comprises a first pulse width different from a second pulse width of the second electrical stimulation pulse.

EXAMPLE 17

The system of any of examples 15 to 16, wherein delivering the first electrical stimulation pulse comprises delivering the first electrical stimulation pulse from a first electrode of the plurality of electrodes, and wherein delivering the second electrical stimulation pulse comprises delivering the second electrical stimulation pulse from a second electrode of the plurality of electrodes, wherein the first electrode is different than the second electrode.

EXAMPLE 18

The system of any of examples 15 to 16, wherein the processing circuitry is configured to control the stimulation generation circuitry deliver the first electrical stimulation pulse by being further configured to control the stimulation generation circuitry to deliver both the first electrical stimulation pulse from an electrode of the plurality of electrodes and the second electrical stimulation pulse from the electrode of the plurality of electrodes.

EXAMPLE 19

The system of example 18, the processing circuitry further configured to control the stimulation generation circuitry to deliver a third electrical stimulation pulse of the plurality of electrical stimulation pulses from a second electrode of the plurality of electrodes subsequent to delivering the second electrical stimulation pulse and prior to delivering the one or more recharge pulses.

EXAMPLE 20

The system of any of examples 15 to 19, the processing circuitry further configured to control the stimulation generation circuitry to withhold the delivery of the one or more recharge pulses for an amount of time following the delivery of the second electrical stimulation pulse.

EXAMPLE 21

The system of any of examples 15 to 20, wherein the processing circuitry is configured to control the stimulation generation circuitry to deliver the one or more recharge pulses by being further configured to control the stimulation generation circuitry to: simultaneously deliver both a first recharge pulse of the one or more recharge pulses for the first electrical stimulation pulse and a second recharge pulse of the one or more recharge pulses for the second electrical stimulation pulse.

EXAMPLE 22

The system of any of examples 15 to 20, wherein the processing circuitry is configured to control the stimulation generation circuitry to deliver the one or more recharge pulses by being further configured to control the stimulation generation circuitry to: deliver a first recharge pulse of the one or more recharge pulses for the first electrical stimulation pulse; and subsequent to delivering the first recharge pulse, deliver a second recharge pulse of the one or more recharge pulses for the second electrical stimulation pulse.

EXAMPLE 23

The system of any of examples 15 to 20, wherein the processing circuitry is configured to control the stimulation generation circuitry to deliver the one or more recharge pulses by being further configured to control the stimulation generation circuitry to: deliver a first recharge pulse of the one or more recharge pulses for the second electrical stimulation pulse; and subsequent to delivering the first recharge pulse, deliver a second recharge pulse of the one or more recharge pulses for the first electrical stimulation pulse.

EXAMPLE 24

The system of any of examples 15 to 20, wherein the processing circuitry is configured to control the stimulation generation circuitry to deliver the one or more recharge pulses by being further configured to control the stimulation generation circuitry to: deliver a recharge pulse of the one or more recharge pulses for both the first electrical stimulation pulse and the second electrical stimulation pulse.

EXAMPLE 25

The system of any of examples 15 to 24, wherein the stimulation generation circuitry generates the plurality of electrical stimulation pulses according to a first stimulation program and second stimulation program saved on a memory, wherein the processing circuitry is further configured to generate the first electrical stimulation pulse according to the first stimulation program and generate the second electrical stimulation pulse according to the second stimulation program.

EXAMPLE 26

A computer readable medium comprising instructions that, when executed by a processor, cause the processor to: generate a plurality of electrical stimulation pulses having a duty cycle in a range of about 5% to about 50%, wherein the plurality of electrical stimulation pulses have a stimulation intensity less than at least one of a perception threshold or a paresthesia threshold of a patient; deliver a first electrical stimulation pulse of the plurality of electrical stimulation pulses to the patient; subsequent to delivering the first electrical stimulation pulse, deliver a second electrical stimulation pulse of the plurality of electrical stimulation pulses to the patient; and subsequent to delivering the first pulse and the second pulse, deliver one or more recharge pulses for at least the first electrical stimulation pulse and the second electrical stimulation pulse.

EXAMPLE 27

The computer readable medium of example 26, wherein the first electrical stimulation pulse comprises a first pulse width different from a second pulse width of the second electrical stimulation pulse.

EXAMPLE 28

The computer readable medium of any of examples 26 to 27, wherein the instructions for delivering electrical stimulation pulses cause the processor to deliver the first electrical stimulation pulse from a first electrode, and wherein delivering the second electrical stimulation pulse comprises delivering the second electrical stimulation pulse from a second electrode, wherein the first electrode is different than the second electrode.

EXAMPLE 29

The computer readable medium of any of examples 26 to 27, wherein the instructions for delivering the electrical stimulation pulses cause the processor to deliver both the first electrical stimulation pulse and the second electrical stimulation pulse from a first electrode.

EXAMPLE 30

The computer readable medium of example 29, wherein the instructions cause the processor to deliver a third electrical stimulation pulse of the plurality of electrical stimulation pulses from a second electrode subsequent to delivering the second electrical stimulation pulse and prior to delivering the one or more recharge pulses.

EXAMPLE 31

The computer readable medium of any of examples 26 to 30, wherein the instructions cause the processor to withhold the delivery of the one or more recharge pulses for an amount of time following the delivery of the second electrical stimulation pulse.

EXAMPLE 32

The computer readable medium of any of examples 26 to 31, wherein the instructions for delivering the one or more recharge pulses cause the processor to simultaneously deliver both a first recharge pulse of the one or more recharge pulses for the first electrical stimulation pulse and a second recharge pulse of the one or more recharge pulses for the second electrical stimulation pulse.

EXAMPLE 33

The computer readable medium of any of examples 26 to 31, wherein the instructions for delivering the one or more recharge pulses cause the processor to: deliver a first recharge pulse of the one or more recharge pulses for the first electrical stimulation pulse; and subsequent to delivering the first recharge pulse, deliver a second recharge pulse of the one or more recharge pulses for the second electrical stimulation pulse.

EXAMPLE 34

The computer readable medium of any of examples 26 to 31, wherein the instructions for delivering the one or more recharge pulses cause the processor to: deliver a first recharge pulse of the one or more recharge pulses for the second electrical stimulation pulse; and subsequent to delivering the first recharge pulse, deliver a second recharge pulse of the one or more recharge pulses for the first electrical stimulation pulse.

EXAMPLE 35

The computer readable medium of any of examples 26 to 31, wherein the instructions for delivering the one or more recharge pulses cause the processor to deliver a recharge pulse of the one or more recharge pulses for both the first electrical stimulation pulse and the second electrical stimulation pulse.

EXAMPLE 36

The computer readable medium of any of examples 26 to 35, wherein instructions cause the processor to generate the first electrical stimulation pulse according to a first stimulation program and generate the second electrical stimulation pulse according to a second stimulation program.

What is claimed is:

1. A system comprising:
stimulation generation circuitry configured to generate and deliver electrical stimulation therapy to a patient; and
processing circuitry configured to control the stimulation generation circuitry to:
generate a plurality of electrical stimulation pulses having a duty cycle in a range of about 5% to about 50%, wherein the plurality of electrical stimulation pulses have a stimulation intensity less than at least one of a perception threshold or a paresthesia threshold of a patient;
deliver a first electrical stimulation pulse of the plurality of electrical stimulation pulses to the patient;
subsequent to delivering the first electrical stimulation pulse, deliver a second electrical stimulation pulse of the plurality of electrical stimulation pulses to the patient; and
subsequent to delivering the first pulse and the second pulse, deliver one or more recharge pulses for at least the first electrical stimulation pulse and the second electrical stimulation pulse.

2. The system of claim 1, wherein the first electrical stimulation pulse comprises a first pulse width different from a second pulse width of the second electrical stimulation pulse.

3. The system of claim 1, wherein the stimulation generation circuitry is configured to deliver the first electrical stimulation pulse by delivering the first electrical stimulation pulse from a first electrode of a plurality of electrodes, and wherein the stimulation generation circuitry is configured to deliver the second electrical stimulation pulse by delivering the second electrical stimulation pulse from a second electrode of the plurality of electrodes, wherein the first electrode is different than the second electrode.

4. The system of claim 1, wherein the processing circuitry is configured to control the stimulation generation circuitry deliver the first electrical stimulation pulse by being further configured to control the stimulation generation circuitry to deliver both the first electrical stimulation pulse from an electrode of the plurality of electrodes and the second electrical stimulation pulse from the electrode of the plurality of electrodes.

5. The system of claim 4, wherein the processing circuitry is further configured to control the stimulation generation circuitry to deliver a third electrical stimulation pulse of the plurality of electrical stimulation pulses from a second electrode of the plurality of electrodes subsequent to delivering the second electrical stimulation pulse and prior to delivering the one or more recharge pulses.

6. The system of claim 1, wherein the processing circuitry is further configured to control the stimulation generation circuitry to withhold the delivery of the one or more recharge pulses for an amount of time following the delivery of the second electrical stimulation pulse.

7. The system of claim 1, wherein the processing circuitry is configured to control the stimulation generation circuitry to deliver the one or more recharge pulses by being further configured to control the stimulation generation circuitry to simultaneously deliver both a first recharge pulse of the one or more recharge pulses for the first electrical stimulation pulse and a second recharge pulse of the one or more recharge pulses for the second electrical stimulation pulse.

8. The system of claim 1, wherein the processing circuitry is configured to control the stimulation generation circuitry to deliver the one or more recharge pulses by being further configured to control the stimulation generation circuitry to:
deliver a first recharge pulse of the one or more recharge pulses for the first electrical stimulation pulse; and
subsequent to delivering the first recharge pulse, deliver a second recharge pulse of the one or more recharge pulses for the second electrical stimulation pulse.

9. The system of claim 1, wherein the processing circuitry is configured to control the stimulation generation circuitry to deliver the one or more recharge pulses by being further configured to control the stimulation generation circuitry to:
deliver a first recharge pulse of the one or more recharge pulses for the second electrical stimulation pulse; and
subsequent to delivering the first recharge pulse, deliver a second recharge pulse of the one or more recharge pulses for the first electrical stimulation pulse.

10. The system of claim 1, wherein the processing circuitry is configured to control the stimulation generation circuitry to deliver the one or more recharge pulses by being further configured to control the stimulation generation circuitry to deliver a recharge pulse of the one or more recharge pulses for both the first electrical stimulation pulse and the second electrical stimulation pulse.

11. The system of claim 1, wherein the stimulation generation circuitry is configured to generate the plurality of electrical stimulation pulses according to a first stimulation program and second stimulation program saved on a memory, and wherein the processing circuitry is further configured to generate the first electrical stimulation pulse according to the first stimulation program and generate the second electrical stimulation pulse according to the second stimulation program.

12. The system of claim 1, wherein the one or more recharge pulses comprises ore or more passive recharge pulses.

13. The system of claim 1, wherein the one or more recharge pulses comprises one or more active recharge pulses having predetermined pulse amplitudes and pulse widths.

14. The system of claim 1, further comprising an implantable medical device comprising the stimulation generation circuitry and the processing circuitry.

15. The system of claim 1, wherein the first electrical stimulation pulse and the second electrical stimulation pulse comprise a first polarity, and wherein the one or more recharge pulses comprise a second polarity opposite the first polarity.

16. A method comprising:
generating, by a medical device, a plurality of electrical stimulation pulses having a duty cycle in a range of about 5% to about 50%, wherein the plurality of electrical stimulation pulses have a stimulation intensity less than at least one of a perception threshold or a paresthesia threshold of a patient;
delivering, by the medical device, a first electrical stimulation pulse of the plurality of electrical stimulation pulses to the patient;
subsequent to delivering the first electrical stimulation pulse, delivering, by the medical device, a second electrical stimulation pulse of the plurality of electrical stimulation pulses to the patient; and
subsequent to delivering the first pulse and the second pulse, delivering, by the medical device, one or more recharge pulses for at least the first electrical stimulation pulse and the second electrical stimulation pulse.

17. The method of claim 16, wherein delivering the first electrical stimulation pulse comprises delivering the first electrical stimulation pulse from an electrode of a lead coupled to the medical device, and wherein delivering the second electrical stimulation pulse comprises delivering the second electrical stimulation pulse from the electrode of the lead, and wherein the method further comprises:
subsequent to delivering the second electrical stimulation pulse and prior to delivering the one or more recharge pulses, delivering, by the medical device, a third electrical stimulation pulse of the plurality of electrical stimulation pulses to the patient from a second electrode coupled to the medical device.

18. The method of claim 16, further comprising, subsequent to delivering the second electrical stimulation pulse and prior to delivering the one or more recharge pulses, delivering, by the medical device, a third electrical stimulation pulse of the plurality of electrical stimulation pulses to the patient from a second electrode coupled to the medical device.

19. The method of claim 16, wherein delivering the one or more recharge pulses further comprises:
delivering, by the medical device, a first recharge pulse of the one or more recharge pulses for the first electrical stimulation pulse; and
subsequent to delivering the first recharge pulse, delivering, by the medical device, a second recharge pulse of the one or more recharge pulses for the second electrical stimulation pulse.

20. A non-transitory computer readable medium comprising instructions that, when executed by processing circuitry, cause the processing circuitry to control stimulation generation circuitry to:

generate a plurality of electrical stimulation pulses having a duty cycle in a range of about 5% to about 50%, wherein the plurality of electrical stimulation pulses have a stimulation intensity less than at least one of a perception threshold or a paresthesia threshold of a patient;

deliver a first electrical stimulation pulse of the plurality of electrical stimulation pulses to the patient;

subsequent to delivering the first electrical stimulation pulse, deliver a second electrical stimulation pulse of the plurality of electrical stimulation pulses to the patient; and subsequent to delivering the first pulse and the second pulse, deliver one or more recharge pulses for at least the first electrical stimulation pulse and the second electrical stimulation pulse.

21. The system of claim 1, wherein the electrical stimulation therapy comprises spinal cord stimulation therapy.

* * * * *